US010758650B1

(12) United States Patent
Lin

(10) Patent No.: US 10,758,650 B1
(45) Date of Patent: *Sep. 1, 2020

(54) CONTROL APPARATUS FOR DELIVERY OF THERAPY TO WOUNDS AND RELATED METHODS OF USE

(71) Applicant: Edward D Lin, Osprey, FL (US)

(72) Inventor: Edward D Lin, Osprey, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/889,542

(22) Filed: Jun. 1, 2020

Related U.S. Application Data

(63) Continuation of application No. 15/663,710, filed on Jul. 29, 2017.

(51) Int. Cl.
| | | |
|---|---|---|
| *A61M 1/00* | (2006.01) | |
| *A61F 13/02* | (2006.01) | |
| *A61F 13/00* | (2006.01) | |
| *A61M 3/02* | (2006.01) | |
| *A61M 35/00* | (2006.01) | |

(52) U.S. Cl.
CPC ..... *A61M 1/0084* (2013.01); *A61F 13/00068* (2013.01); *A61F 13/0216* (2013.01); *A61M 1/0052* (2014.02); *A61M 1/0088* (2013.01); *A61M 3/02* (2013.01); *A61M 3/022* (2014.02); *A61M 3/0208* (2014.02); *A61M 3/0212* (2014.02); *A61M 3/0216* (2014.02); *A61M 35/30* (2019.05); *A61M 1/0037* (2013.01); *A61M 2202/0208* (2013.01); *A61M 2202/0275* (2013.01); *A61M 2202/0283* (2013.01); *A61M 2205/3337* (2013.01); *A61M 2205/3344* (2013.01); *A61M 2205/50* (2013.01); *A61M 2205/75* (2013.01); *A61M 2205/8206* (2013.01)

(58) Field of Classification Search
CPC ...... A61F 13/00068; A61F 2013/00536; A61F 2013/0054; A61M 1/009; A61M 1/0088; A61M 1/0023; A61M 1/0025; A61M 1/0031; A61M 1/0037; A61M 1/0084
See application file for complete search history.

(56) References Cited

U.S. PATENT DOCUMENTS

| | | | | |
|---|---|---|---|---|
| 8,187,237 B2* | 5/2012 | Seegert | ................. | A61M 27/00 604/313 |
| 8,529,548 B2* | 9/2013 | Blott | ................. | A61F 13/00063 604/543 |
| 2007/0118096 A1* | 5/2007 | Smith | .................... | A61B 5/445 604/541 |

* cited by examiner

*Primary Examiner* — Laura A Bouchelle
(74) *Attorney, Agent, or Firm* — Cardle Patent Law CHTD

(57) ABSTRACT

In various aspects, the wound therapy apparatus disclosed herein includes a wound interface that defines an enclosed space over a wound bed that is fluid tight when secured to a skin surface around the wound bed. The wound therapy apparatus includes a control group that cooperates with the wound interface to regulate input of input fluid comprising a gas having an $O_2$ concentration greater than atmospheric air into the enclosed space and to regulate the withdrawal of output fluid from the enclosed space in order to vary an actual pressure $p_a$ within the enclosed space generally between a minimum pressure $p_{min}$ and a maximum pressure $p_{max}$. Related methods of use of the wound therapy apparatus are disclosed herein.

17 Claims, 17 Drawing Sheets

CONTROL APPARATUS FOR DELIVERY OF THERAPY TO WOUNDS AND RELATED METHODS OF USE

CROSS-REFERENCE TO RELATED APPLICATIONS

This application is a continuation of co-pending U.S. patent application Ser. No. 15/663,710 filed 29 Jul. 2017 which is hereby incorporated by reference in its entirety.

BACKGROUND OF THE INVENTION

Field

The present disclosure relates to medical devices, and, more particularly, to apparatus and related methods for delivering therapy to wound beds.

Related Art

A wound bed, as used herein, includes a localized region of tissue that has lost skin and been affected by hostile factors resulting in, for example, cellular abnormalities such as swelling, inflammation, degradation, infection, or cell death. The wound bed may include varying degrees of exposure of underlying layers and structures along with possible infections and tissue changes. The wound bed represents an unhealed wound. In contrast, a healed wound is a skin surface that was previously injured but the focal breach is now entirely sealed and covered by varying amounts of epidermis and scar tissue. The wound bed may lie within a wound boundary that extends around the affected region on the skin surface of the skin. The wound bed may extend contiguously in depth within the dermis, and the wound bed may extend subcutaneously, for example, into fat, muscle, or beyond. Thus, the wound bed may include undermined flaps, sinuses, tunnels, and fistulae and the surrounding affected tissues. An example of a wound bed including some reference anatomy is illustrated in FIG. 1. Wound boundary, as used herein, refers to the boundary of the wound bed at the skin surface of the skin.

Various negative pressure wound therapy (NPWT) devices currently used for treatment of wound bed include a dressing, a cover made of a flexible sheet of polymer and covered, at least in part, with adhesive, and an evacuation tube. In order to use current NPWT devices, the wound bed is packed with the dressing and the evacuation tube is placed about the dressing. The cover is then placed over the wound bed and attached adhesively to the skin surface around the wound bed to seal the wound bed, dressing, and evacuation tube in place. Finally, air within the region between the sheet and the wound bed is evacuated through the evacuation tube, which is in fluid communication with the dressing, to produce a suction pressure $p_s$ within an enclosed space between the cover and the wound bed that is less than the ambient pressure $p_{amb}$. The wound bed and surrounding skin are as the suction pressure $p_s$ is decreased below the ambient pressure $p_{amb}$. Exudate from the wound bed may be transmitted through the dressing and then evacuated through the evacuation tube. The wound may be subjected to a suction pressure $p_s$, that is static and typically between around −80 mm Hg to around −175 mm Hg below ambient pressure $p_{amb}$.

The suction pressure $p_s$ may be maintained statically continually for weeks, if not months, until end of therapy, except during dressing changes. Because capillaries are exceedingly thin-walled microscopic tubules, capillaries are easily collapsed shut by the suction pressure. Studies have shown that while blood flow increases in proportion to suction pressure $p_s$ at a further distance of 2.5 cm from the wound edge, blood flow is diminished detrimentally by at least as much closer to the wound bed, at 0.5 cm from the wound edge where increased blood flow is most needed.

It has thus become recognized that it may be beneficial to relieve the suction pressure $p_s$ from time to time in order to allow capillaries adjacent to the wound bed to refill. However, the relief of the suction pressure $p_s$, if at all provided, is accomplished in current NPWT devices by input of atmospheric air into the enclosed space between the covering and the wound bed. The suction pressure $p_s$ may be relieved only to $p_{amb}$−25 mm Hg instead of to $p_{amb}$ in order to maintain the cover in sealing securement over the wound bed. Such relief of the suction pressure $p_s$ in some devices may occur only intermittently, or not at all.

The average time to healing for a chronic wound is almost 6 months, attesting to the challenges of getting enough blood flow and oxygen to the wound bed to enable healing. NPWT requires skilled nursing and physician supervision, and is unable to salvage all wounds. Tens of thousands of deaths due to wound-related complications and 80,000 limb amputations per year occur in the US, each of which represent many months, if not years of failed costly therapy. Globally, there are 1 million amputations a year. NPWT may be tedious to apply and dressing changes, which occur usually every other day, are typically excruciatingly painful because of the tearing off of granulation tissue embedded in the dressing that occurs with each dressing change. Such disruption to the granulation tissue may set back the healing process. About 66% of wound beds require 15 weeks of NPWT while another 10% require 33 weeks or more of NPWT to heal.

In addition, the evacuation tube may become clogged by the proteinaceous exudate, which may result in interruption of the NPWT. The suction pressure $p_s$ may be inaccurately sensed, falsely indicating that suction pressure $p_s$ is at the desired level when in fact, due to exudate plug, there is little or no suction pressure within the enclosed space over the wound bed. Because the dressing is tedious to apply and painful to remove, as a practical matter, it is deemed not feasible to take it off repeatedly in order to attach other devices to deliver other therapies.

NPWT has been combined with instillation of an antibiotic solution in order to treat extra difficult wound beds. This system interposes one or more episodes of liquid therapy a few times a day in which the solution is introduced to the wound bed and allowed to "dwell" for a period of time and then removed. This "NPWT with instillation" requires a premeasurement of the volume of the wound bed, entering that volume into the infusion pump so that no excessive amount of instillation takes place that could jeopardize the integrity of the seal of the cover around the wound. Extra time, equipment and skilled attention is required to administer NPWT combined with instillation.

Another type of wound therapy in common use is total body hyperbaric oxygen (HBO). The patient is placed in a hyperbaric chamber and exposed, typically, to 2.5 ATA (atmospheres Absolute) of medically pure oxygen for 90 minutes. Exposure past 120 minutes increases the risk of oxygen toxicity, probably due to the increased formation of superoxide, $H_2O_2$ or other oxidizing free radicals. Seizures and other serious consequences may result. Such a 90-minute session avails oxygen enrichment to the wound bed for a mere 6% of a day. The Medicare branch of the US Government usually approves HBO treatment for 30-40 sessions at a time at a cost per session of many hundreds to $1,000. This underscores not only the high cost of chronic wound care and HBO's low ability to effect healing with just a few sessions, but also the general lack of more efficacious therapeutic modalities.

Therefore, for at least these reasons, it is evident that there is a strong and unmet need for improved apparatus for delivering wound therapy as well as related methods of wound therapy.

BRIEF SUMMARY OF THE INVENTION

These and other needs and disadvantages may be overcome by the wound therapy apparatus and related method of use disclosed herein. Additional improvements and advantages may be recognized by those of ordinary skill in the art upon study of the present disclosure.

In various aspects, the wound therapy apparatus disclosed herein includes a wound interface that defines an enclosed space over a wound bed that is fluid tight when secured to a skin surface around the wound bed. The wound therapy apparatus includes a control group that cooperates with the wound interface to regulate input of input fluid comprising a gas having an $O_2$ concentration greater than atmospheric air into the enclosed space and to regulate the withdrawal of output fluid from the enclosed space in order to vary an actual pressure $p_a$ within the enclosed space generally between a minimum pressure $p_{min}$ and a maximum pressure $p_{max}$ the minimum pressure $p_{min}$ being less than ambient pressure $p_{amb}$, in various aspects. The input of the gas having an $O_2$ concentration greater than atmospheric air is sequential with withdrawal of the gas having an $O_2$ concentration greater than atmospheric air, in various aspects.

In various aspects, the wound therapy apparatus disclosed herein includes a liquid source of liquid, a gas source of gas having an $O_2$ concentration greater than that of atmospheric air, and a wound interface engaged with a skin surface around a wound bed to define an enclosed space about the wound bed, the enclosed space being fluid tight. The wound therapy apparatus includes a control group in operable communication with the liquid source, the gas source, and the enclosed space to selectively input liquid and gas into the enclosed space and to regulate the withdrawal of output fluid from the enclosed space, in various aspects.

Related methods of use of the wound therapy apparatus disclosed herein may include the step of engaging a wound interface with a skin surface around a wound bed thereby defining an enclosed space, and the step of regulating the input of input fluid into the enclosed space in sequence with regulating the withdrawal of output fluid from the enclosed space using a control group thereby altering periodically the actual pressure $p_a$ within the enclosed space according to a pressure cycle of a target pressure $p_0$, in various aspects. The pressure cycle has a minimum pressure $p_{min}$ and a maximum pressure $p_{max}$, and the input fluid comprises a gas having an $O_2$ concentration greater than atmospheric air, in various aspects.

This summary is presented to provide a basic understanding of some aspects of the methods and apparatus disclosed herein as a prelude to the detailed description that follows below. Accordingly, this summary is not intended to identify key elements of the apparatus and methods disclosed herein or to delineate the scope thereof.

Figure 1:
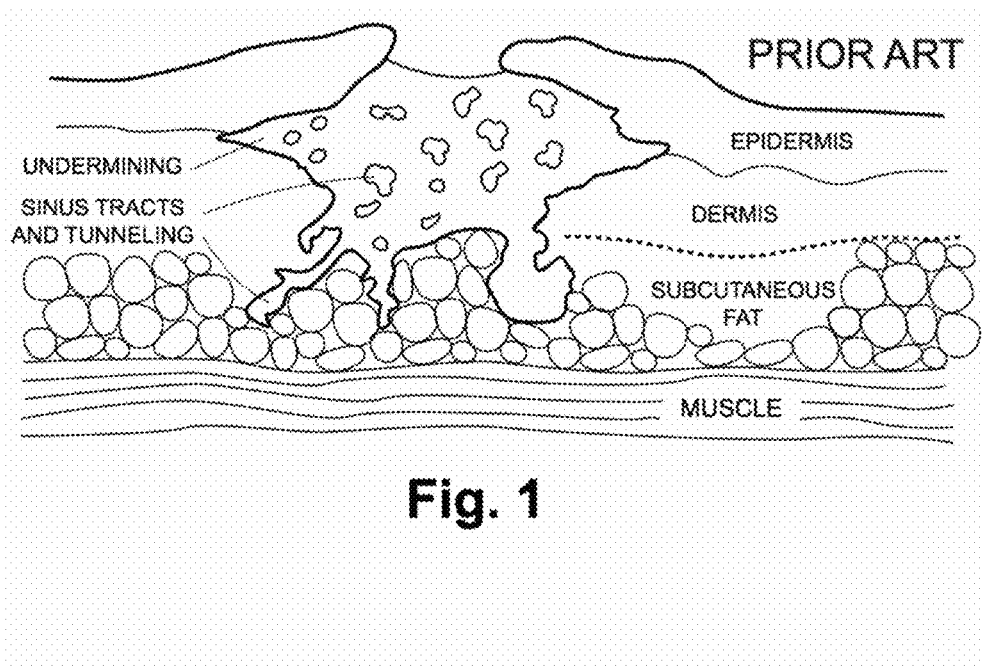
FIG. 1 by cross-sectional view an exemplary wound bed that demonstrates undermining, wound tunneling, and fistulae.

The Figures are exemplary only, and the implementations illustrated therein are selected to facilitate explanation. The number, position, relationship and dimensions of the elements shown in the Figures to form the various implementations described herein, as well as dimensions and dimensional proportions to conform to specific force, weight, strength, flow and similar requirements are explained herein or are understandable to a person of ordinary skill in the art upon study of this disclosure. Where used in the various Figures, the same numerals designate the same or similar elements. Furthermore, when the terms "top," "bottom," "right," "left," "forward," "rear," "first," "second," "inside," "outside," and similar terms are used, the terms should be understood in reference to the orientation of the implementations shown in the drawings and are utilized to facilitate description thereof. Use herein of relative terms such as generally, about, approximately, essentially, may be indicative of engineering, manufacturing, or scientific tolerances such as ±0.1%, ±1%, ±2.5%, ±5%, or other such tolerances, as would be readily recognized by those of ordinary skill in the art upon study of this disclosure.

DETAILED DESCRIPTION OF THE INVENTION

A wound therapy apparatus and related methods of wound therapy are disclosed herein. In various aspects, the wound therapy apparatus includes a wound interface engaged with a skin surface around a wound bed to define an enclosed space over the wound bed, the enclosed space being fluid tight. A control group cooperates with the wound interface to regulate input of input fluid into the enclosed space and to regulate the withdrawal of output fluid from the enclosed space in order to vary an actual pressure $p_a$ within the enclosed space generally between a minimum pressure $p_{min}$ and a maximum pressure $p_{max}$, in various aspects. The minimum pressure $p_{min}$ is less than ambient pressure $p_{amb}$, and the input of the gas is sequential with withdrawal of the gas having an $O_2$ concentration greater than atmospheric air, in various aspects. The control group may vary periodically the actual pressure $p_a$ within the enclosed space in a pressure cycle between the minimum pressure $p_{min}$ and the maximum pressure $p_{max}$. The gas may have an $O_2$ concentration greater than atmospheric air (about 20.95% by volume or about 0.2095 mole $O_2$ per mole of dry air), Fluid, as used herein, includes, liquid(s), gas(ses), and combinations thereof. Liquid includes, for example, saline solution, Dakin's solution, proteolytic enzyme solution, biofilm degradation solution, cytokines, antibiotic lavage, amniotic fluid, platelet-enriched plasma, antibiotic, analgesic, anesthetic, and combinations thereof. Liquid may include saline or water based solutions that, for example, irrigate the wound bed, remove bio-burden, or moisturize the wound bed.

Gas may include, for example, air, oxygen, nitric oxide, nitrogen, or suitable therapeutic or inert gasses, and combinations thereof. Gas, for example, may be nitric oxide diluted in nitrogen at about 200 ppm to about 800 ppm. Gas input into the enclosed space to increase the actual pressure $p_a$ within the enclosed space from the minimum pressure $p_{min}$ to the maximum pressure $p_{max}$ may have an $O_2$ concentration greater than atmospheric air (about 21.95% by volume), in various aspects. In various aspects, the gas may be medical grade oxygen. Medical grade oxygen may conform to certain standards, for example, United States Food and Drug Administration standards or other appropriate regulatory standards. In various aspects, the medical grade oxygen may be United States Pharmacopoeia grade oxygen. In various other implementations, input fluid 16 supplied to wound interface 115 may be a liquid that may have some therapeutic benefit.

Sequential withdrawal of output fluid from the enclosed space and input of input fluid into the enclosed space means that withdrawal of output fluid and the input of input fluid does not occur simultaneously. Input fluid may be being input into the enclosed space or output fluid may be being withdrawn from the enclosed space but not the input of input fluid simultaneously with output of output fluid. An exception may be when the input fluid is a liquid and the liquid is input and withdrawn simultaneously, for example, during irrigation of the wound bed. Simultaneous input of liquid may irrigate or flush the wound bed with an amount of liquid several times the volume of the enclosed space to cleanse the wound bed of, for example, microbes, cellular debris, and biofilm.

Using the "downtime" of the relief phase of NPWT for programmed delivery of oxygen or other therapeutic fluids including gases and liquids into the enclosed space may effectively result in a substantial amount of new beneficial therapy in a 24-hour span where previously not even suction therapy existed. The net result is the even, regular addition of many new extra hours of beneficial therapy interspersed between suction pressure therapy that may accelerate healing through synergistic effects. Because chronic wound healing is already extremely protracted, lasting on average 23 weeks, the ability to add important needed therapy each and every day—without reducing the duration of the fundamental pressure therapy—may serve as a de novo creation of additional synergies that may accelerate healing. For example, consider a pressure cycle having a 6-minute duration with pressure $p_0$ at $p_{min}$ for 4 minutes and the pressure $p_0$ is relieved to $p_{max}$ for 2 minutes (i.e., ⅓ of the duration of the negative pressure cycle is pressure relief). In this example, $p_{max}$ may be around ambient pressure $p_{amb}$ or greater. Using fluid with $O_2$ concentration greater than atmospheric air results in 2 minutes of topical oxygen therapy around ambient or higher pressure in this example. Ten 2-minute cycles of such topical oxygen therapy per hour add up to 240 cycles daily that equals 8 hours per day of topical oxygen therapy without decreasing the amount of negative pressure therapy delivered. This may deliver additional therapy without displacing or shortening the fundamental underlying pressure therapy. Note that $p_{min}$, $p_{max}$ and $p_{amb}$ are approximate and relative, and may vary from cycle to cycle depending on apparatus and environmental factors including altitude. The therapeutic results are substantially achieved regardless whether the target pressures are attained exactly or approximated.

As a second example, the pressure cycle has a 6-minute duration with pressure $p_0$ at $p_{min}$ for 3 minutes and the pressure relieved to $p_{max}$ for 3 minutes (½ of the duration of the pressure cycle), which results in delivery of topical oxygen therapy to the wound bed around ambient pressure or higher totaling 12 hours per day. Therefore, towards the latter healing phase when edema and exudation is greatly diminished such that negative pressure $p_{min}$ is needed less, the duration of topical oxygen can be correspondingly increased to accelerate the next phase of healing.

In various aspects, every nth pressure cycle (where n is any suitable number such as 2 through 60 or even 120 or more) is relieved with a liquid.

The methods of wound therapy include, in various aspects, providing a therapy regimen to the wound bed within an enclosed space, the therapy regimen comprising delivering consecutively a number of pressure cycles of an actual pressure $p_a$ within the enclosed space, each pressure cycle generally comprising a pressure range $p_{min} \leq p_a \leq p_{max}$ where $p_{min} \leq p_{amb}$ and $p_{amb} \leq p_{max}$ with $p_{min} < p_{max}$ and $p_{amb}$ is the ambient pressure, an input fluid comprising gas(es) and liquids being introduced into the enclosed space as each pressure cycle progresses from $p_{min}$ to $p_{max}$. Pressures $p_{min}$, $p_{max}$, and the duration of the pressure cycle as well as the fluid(s) introduced into the enclosed space may vary from pressure cycle to pressure cycle depending on the desired therapeutic goal desired.

In various aspects, the methods of wound therapy may include the step of engaging a wound interface with a skin surface around a wound bed thereby defining an enclosed space. In various aspects, the methods of wound therapy may include the step of regulating the input of input fluid into the enclosed space in sequence with regulating the withdrawal of output fluid from the enclosed space using a control group thereby altering periodically the actual pressure $p_a$ within the enclosed space generally according to a pressure cycle of a target pressure $p_0$, the pressure cycle having a minimum pressure $p_{min}$ and a maximum pressure $p_{max}$, the input fluid comprising a gas having an $O_2$ concentration greater than atmospheric air. In various aspects, the methods of wound therapy may include the step of removing exudate from the enclosed space by flowing the output fluid to a reservoir. In various aspects, the input fluid may be a liquid in which case the input of the input liquid and the output of the output liquid may occur sequentially or simultaneously depending the therapeutic goal. In various aspects, the methods of wound therapy may include the step of receiving data from a user with an I/O interface; and communicating the data from the user I/O to a controller thereby altering targeted aspects of the pressure cycle. In various aspects, the methods of wound therapy may include the step of delivering a therapy regimen to the wound bed, the therapy regimen comprising a series of pressure cycles of the actual pressure $p_a$ within the enclosed space.

By inputting gas with $O_2$ concentration greater than that found in atmospheric air into the enclosed space during portions of the pressure cycle in certain aspects, the resulting $O_2$ enrichment may resuscitate the hypoxic wound cells, may sustain the revived cells in cell division and collagen synthesis, may inhibit the growth of anaerobic bacteria, may enhance the efficacy of antibiotics, and may enhance survival of stem cells and tissue grafts, and augment the therapeutic benefits of other bioengineered materials. Furthermore, such $O_2$ enrichment provided to the wound bed may be beneficial because the $O_2$ enrichment is [1] under a favorable concentration gradient, [2] at a favorable pressure gradient that does not impede baseline arterial perfusion (such as between 20-60 mm Hg, but may be higher for brief durations), and [3] during a period of relative reflex hyperemia in regions of tissue where capillaries may have previously been collapsed under suction. The result is the maximum absorption and uptake of oxygen under increased-flow condition. Additionally, in aspects wherein the fluid-tight enclosed space provides a hyperbaric condition, the amplitude and period of the $O_2$ delivery may additionally serve and be programmed to provide a form of external pulsation of pressurized $O_2$, with beneficial circulatory effect akin in some respects to providing external CPR to the wound bed.

In various aspects, the methods of wound therapy may include the step of inputting liquid into the enclosed space and may include the step of withdrawing liquid from the enclosed space. The methods of wound therapy may include lavage of the wound bed using liquid input into the enclosed space and withdrawn from the enclosed space in sequence. The method of wound therapy may include providing a therapy to the wound bed by inputting liquid having therapeutic properties into the enclosed space. The therapeutic properties may include, for example, proteolytic, analgesic, antimicrobial, or healing properties. Similarly, and in various aspects, if the goal is one of achieving rapid-flow irrigation, then the liquid input and output with respect to the enclosed space may occur simultaneously instead of sequentially.

Ambient pressure $p_{amb}$, as used herein, refers to the pressure in a region surrounding the wound therapy apparatus. Ambient pressure $p_{amb}$, for example, may refer to atmospheric pressure, hull pressure within an aircraft where the wound therapy apparatus is being utilized, or pressure maintained generally within a building or other structure where the wound therapy apparatus is being utilized. Ambient pressure $p_{amb}$ may vary, for example, with elevation or weather conditions. Pressure $p_{min}$ refers to the minimum pressure achieved within the enclosed space of the wound therapy apparatus, and periodically varying of pressure $p_0$, pressure variation, varying pressure, and similar term refer to changes of pressure $p_0$ within the enclosed space over time, in various aspects. Pressure $p_{max}$ refers to the maximum pressure achieved within the enclosed space of the wound therapy apparatus. Exudate, as used herein, includes, for example, proteinaceous liquids exuded from the wound bed, along with various plasma and blood components and other bodily fluids. Exudate may additionally include waste liquids such as irrigation liquid.

The term fluid-tight or related terms, as used herein, means sufficiently leak-resistant to allow insufflation or vacuum suction to create actual pressure $p_a$ within the enclosed space of a wound interface that may be above or below ambient pressure $p_{amb}$, or to substantially retain fluids including both gasses and liquids within the enclosed space other than by passage through one or more lumen that may fluidly communicate with the enclosed space, in some aspects. The term fluid-tight or related terms, as used herein, means sufficiently leak-resistant to allow insufflation or vacuum suction to maintain actual pressure $p_a$ within the enclosed space of a wound interface t above or below ambient pressure $p_{amb}$, in various aspects.

As used herein the terms distal and proximal are defined from the point of view of a user, such as a physician, nurse, or medical technician, treating a patient with a wound therapy apparatus. A distal portion of the wound therapy apparatus is oriented toward the patient while a proximal portion of the wound therapy apparatus is oriented toward the healthcare provider. A distal portion of a structure may be closest to the patient while a proximal portion of the structure may be closest to the user treating the patient.

As used herein, a wound interface that is deformation resistant resists collapse and substantially maintains its shape, including defining an enclosed space within sufficient to draw a portion of wound bed towards or into the enclosed space, including the wound bed occupying the enclosed space, when subjected to actual pressure $p_a \leq p_{amb}$, in various aspects. In some aspects, at least portions of the wound interface that defines the enclosed space may be essentially rigid. The wound interface, in various aspects, is sufficiently deformation resistant to remain sealingly secured to skin surface and fluid-tight over pressure range $p_{min} \leq p_a \leq p_{max}$.

Apparatus, related methods of use, and related compositions of matter disclosed herein may be implemented, at least in part, in software having the form of computer readable instructions operably received by one or more computers to cause, at least in part, the one or more computers to function as the apparatus or to implement the steps of the methods of use. The methods of use disclosed herein may be implemented as a combination of hardware and operatively received software, in various aspects. Compositions of matter disclosed herein include non-transient computer readable media operably received by the one or more computers to cause the one or more computers, at least in part, to function as the apparatus or to implement the steps of the methods of use.

A computer, as used herein, includes, a processor that may execute computer readable instructions operably received by the processor. The computer may be, for example, a single-processor computer, multiprocessor computer, multi-core computer, minicomputers, mainframe computer, supercomputer, distributed computer, personal computer, hand-held computing device, tablet, smart phone, and a virtual machine, and the computer may include several processors in networked communication with one another. The computer may include memory, screen, keyboard, mouse, storage devices, I/O devices, and so forth, in various aspects, that may be operably connected to a network. The computer may execute various operating systems (OS) such as, for example, Microsoft Windows, Linux, UNIX, MAC OS X, real time operating system (RTOS), VxWorks, INTEGRITY, Android, iOS, or a monolithic software or firmware implementation without a defined traditional operating system.

Network, as used herein, may include the Internet cloud, as well as other networks of local to global scope. The network may include, for example, data storage devices, input/output devices, routers, databases, computers including servers, mobile devices, wireless communication devices, cellular networks, optical devices, cables, and other hardware and operable software, as would be readily recognized by those of ordinary skill in the art upon study of this disclosure. Network may be wired (e.g. optical, electromagnetic), wireless (e.g. infra-red (IR), electromagnetic), or a combination of wired and wireless, and the network may conform, at least in part, to various standards, (e.g. Bluetooth®, FDDI, ARCNET IEEE 802.11, IEEE 802.20, IEEE 802.3, IEEE 1394-1995, USB).

Figure 2:
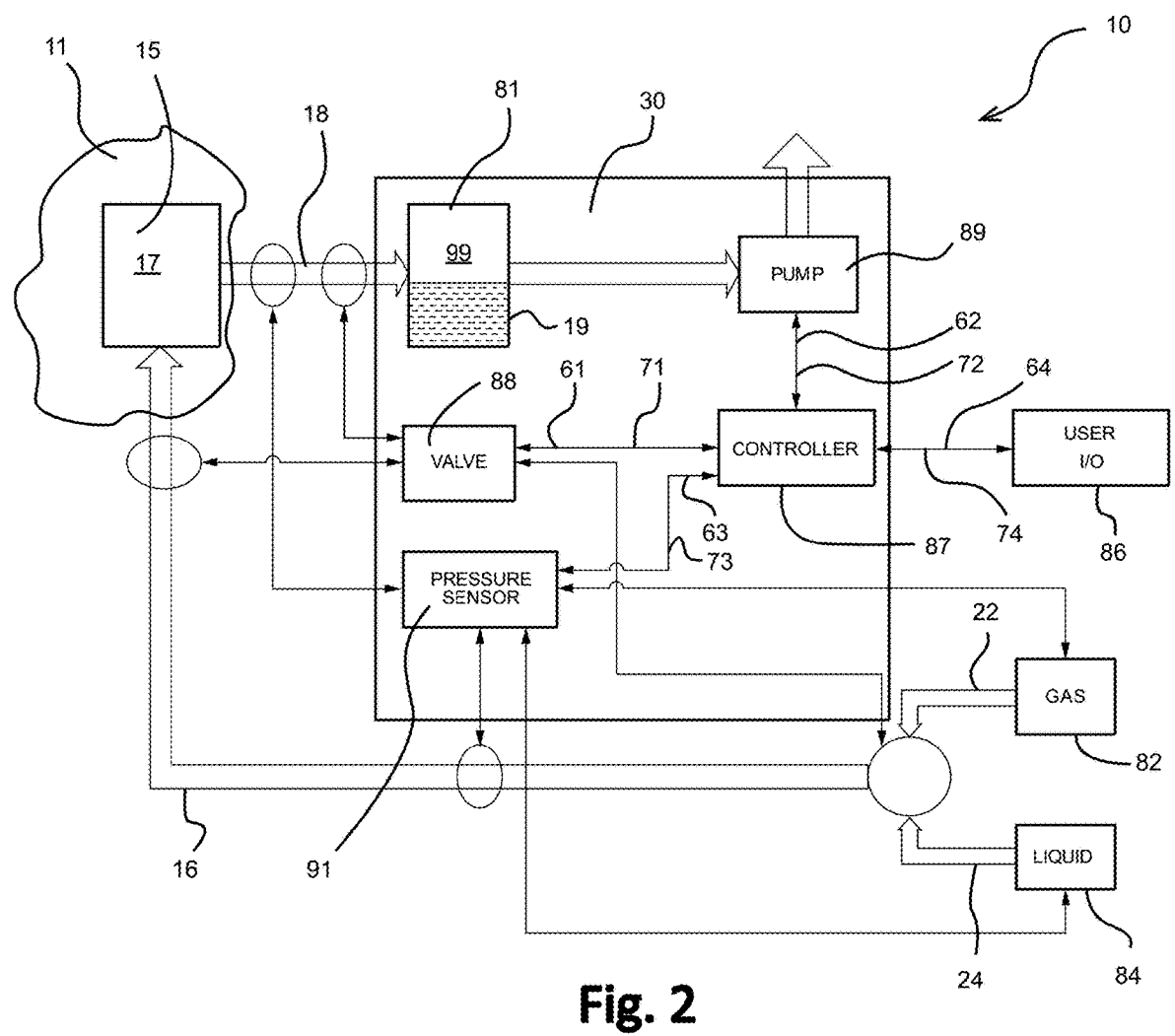
FIG. 2 illustrates by schematic diagram an exemplary implementation of a wound therapy apparatus.

FIG. 2 illustrates exemplary wound therapy apparatus 10. As illustrated in FIG. 2, wound interface 15 is secured to skin surface 11 to define enclosed space 17 that is fluid tight over a wound bed, such as wound bed 213, 313, 413. In this implementation, wound therapy apparatus 10 includes gas source 82 and liquid source 84 in fluid communication with enclosed space 17 of wound interface 15. As illustrated in FIG. 2, wound therapy apparatus 10 includes control group 30, and control group 30 includes controller 87, user I/O 86, valve 88, pump 89, and pressure sensor 91. Control group 30 regulates the communication of gas 22 from gas source 82, liquid 24 from liquid source 84, or combinations of gas 22 and liquid 24 into enclosed space 17 as input fluid 16, as illustrated. Control group 30 regulates the withdrawal of output fluid 18 from enclosed space 17, and output fluid 18 may include, for example, input fluid 16 and exudate 19 as well as air evacuated from enclosed space 17 following attachment of wound interface 15 to skin surface 11, as illustrated. It should be recognized that controller 87, user I/O 86, valve 88, pump 89, and pressure sensor 91 are grouped into control group 30 for explanatory purposes only, in this implementation, and that no spatial or other physical organization or proximity of controller 87, user I/O 86, valve 88, pump 89, and pressure sensor 91 with respect to one another or with respect to gas source 82, liquid source 84 or wound interface 15 is implied by virtue of being grouped into control group 30.

Controller 87 communicates operably with user I/O 86 via communication pathway 64 to communicate data 74 with user I/O 86. Controller 87 communicates operably with valve 88, pump 89, and pressure sensor 91 via communication pathways 61, 62, 63 to control operations of valve 88, pump 89, pressure sensor 91, respectively, at least in part in response to data 74 received by controller 87 from user I/O 86 in order to alter pressure $p_0$ within enclosed space 17, for example, according to exemplary pressure cycle 500, 550, 600, 650, 700, 750, 800, 850, 900, 950 (see FIGS. 9A, 9B, 9C, 9D, 9E, 9F, 9G, 9H, 9I, 9J, respectively) by regulating the input of input fluid 16 into enclosed space 17 and the withdrawal of output fluid 18 from enclosed space 17. Controller 87 may control operations of valve 88, pump 89, pressure sensor 91 at least in part in response to data 74 received from user I/O 86, for example, to deliver Therapy Regimen 1, 2, 3 or 4, to the wound bed enclosed by wound interface 15 (see Example 1). The user may select the pressure cycle, such as pressure cycle 500, 550, 600, 650, 700, 750, 800, 850, 900, 950, and the user may select the therapy regimen, such as Therapy Regimen 1, 2, 3 or 4, using user I/O 86.

Controller 87 controls the operation of wound therapy apparatus 10, at least in part, based upon data 74 communicated to controller 87 from user I/O 86. Controller 87 may control the operation of wound therapy apparatus 10, at least in part, based upon data 71, 72, 73 communicated between controller 87 and valve 88, pump 89, and pressure sensor 91, respectively. Valve 88 and pressure sensor 91 are illustrated as a single valve and a single pressure sensor in this exemplary implementation for explanatory purposes. Is should be recognized that valve 88 may include one or more valves variously disposed about wound therapy apparatus 10 and that pressure sensor 91 may include one or more pressure sensors variously disposed about wound therapy apparatus 10, as would be readily recognized by those of ordinary skill in the art upon study of this disclosure. Controller 87 may include, for example, a processor, memory, software operably communicating with the microprocessor, A/D converter, D/A converter, clock, I/O connectors, and so forth, and controller 87 may be configured for example, as a single chip or as an array of chips disposed about a circuit board, as would be readily recognized by those of ordinary skill in the art upon study of this disclosure. In some implementations, controller 87 may be configured as software operatively received by a computer, and the computer may be, at least in part, located remote, for example, from valve 88, pump 89, and pressure sensor 91.

User I/O 86 may include various switches, push buttons, dials, sliders, graphs, and so forth, whether virtual or physical, for obtaining data 74 from the user that are then communicated to controller 87 in order to allow the user to direct the operation of wound therapy apparatus 10 including pressure cycles of pressure $p_0$ within enclosed space 17 and the delivery of various therapy regimens. In certain implementations, user I/O 86 may be formed as software operably received by a computer. Controller 87 may communicate data 74 to user I/O 86 indicative of the operation of wound therapy apparatus 10, and user I/O 86 may display data 74 to the user.

As illustrated in FIG. 2, gas source 82 fluidly communicates gas 22 and liquid source 84 fluidly communicates liquid 24 with enclosed space 17 of wound interface 15 as input fluid 16 controlled by controller 87 using valve 88. For example, as controlled by controller 87, valve 88 may select gas 22 from gas source 82, liquid 24 from liquid source 84, or combinations of gas 22 from gas source 82 and liquid 24 from liquid source 44 as input fluid 16 for input into enclosed space 17, and valve 88 may regulate, at least in part, the input of input fluid 16 into enclosed space 17 of wound interface 15. Gas source 82 may be, for example, a cylinder of gas including oxygen, an oxygen bag, an oxygen generator, or mains gas including mains oxygen. Liquid source 84 may be, for example, a container of liquid 24 or mains supply of liquid 24.

As illustrated in FIG. 2, output fluid 18 withdrawn from enclosed space 17 passes through reservoir 81, and reservoir 81 captures exudate 19 or liquid, such as liquid 24, from output fluid 18 in chamber 99 of reservoir 81. Gaseous portions of output fluid 18 or gas displaced from chamber 99 of reservoir 81 by capture of liquid 24 or exudate 19 therein may then be vented to the atmosphere from pump 89. Valve 88, pump 89, or valve 88 in combination with pump 89 may regulate the withdrawal of output fluid 18 from enclosed space 17 of wound interface 15 under control of controller 87. Reservoir 81 may be omitted when the quantity of exudate 19 is minimal or there is no liquid, such as liquid 24, in output fluid 18.

Liquid 24 may be withdrawn from enclosed space 17 at least in part by chamber pressure $p_r$ within chamber 99 of reservoir 81 when chamber pressure $p_r$ is less than ambient pressure $p_{amb}$. Chamber 99, which may be disposable and replaceable, provides storage for liquid 24 flowed through enclosed space 17 so that a volume of liquid 24 generally equal to the volume of chamber 99 may be flowed through enclosed space 17 and collected in chamber 99. When pump 89 is OFF and chamber pressure $p_r$ is less than ambient pressure $p_{amb}$, the chamber pressure $p_r$ decreases toward ambient pressure $p_{amb}$ as liquid 24 withdrawn from enclosed space 17 is collected in chamber 99. Liquid input into enclosed space 17 may be stopped, for example, when chamber pressure $p_r$ reaches some set point below ambient pressure $p_{amb}$, say −10 mm Hg, or when liquid 24 fills a certain portion of chamber 99 in order to prevent excessive pressure p0 within enclosed space 17 that may breach the sealing attachment of wound interface 15 to skin surface 11.

As indicated graphically in FIG. 2, valve 88 operably communicates with gas 22, liquid 24, input fluid 16, and output fluid 18. Accordingly, in this illustrated implementation, valve 88 may include one or more valves disposed about wound therapy apparatus to select input fluid 16 as gas 22, liquid 24, combinations of gas 22 and liquid 24, to regulate, at least in part, the input of input fluid 16 into enclosed space 17 of wound interface 15, and to regulate, at least in part, the withdrawal of output fluid 18 from enclosed space 17 of wound interface 15. Data 71 may control the operation of valve 88 and data 71 may be indicative of the operation of valve 88. For example, data 71 may position valve 88 from an open position to a closed position, or data 71 may indicate that valve 88 is in the open position or in the closed position.

As indicated graphically in FIG. 2, pressure sensor 91 operably communicates with gas 22, liquid 24, input fluid 16, and output fluid 18, and enclosed space 17. Pressure sensor 91 may include one or more pressure sensors operable, for example, to detect pressure at various locations in gas 22, liquid 24, input fluid 16, output fluid 18, gas source 82, liquid source 24, or enclosed space 17 of wound interface 15. Pressure sensor 91 may communicate data 73 indicative of the pressure at various locations in gas 22, liquid 24, input fluid 16, output fluid 18, gas source 82, liquid source 24, or enclosed space 17 to controller 87, and controller 87 may alter the operation of valve 88 or pump 89 in response to data 73 from pressure sensor 91. In particular, controller may control valve 88 or pump 89 to maintain the actual pressure $p_a$ within enclosed space 17 generally between a minimum pressure min and a maximum pressure $p_{max}$ and may vary the actual pressure $p_a$ within enclosed space 17 according to a pressure cycle, such as pressure cycle 500, 550, 600, 650, 700, 750, 800, 850, 900, 950 as described in FIGS. 9A, 9B, 9C, 9D, 9E, 9F, 9G, 9H, 9I, 9J, respectively. When $p_a$ within enclosed space 17 exceeds maximum pressure $p_{max}$ output fluid 18 may be withdrawn from enclosed space 17 and gaseous portions of output fluid may be vented to the atmosphere by control group 30. As another example, if liquid 24 is input as input fluid 16 to increase the actual pressure $p_a$ within the enclosed space above the minimum pressure $p_{min}$, the control group may halt input of liquid 24 once the actual pressure $p_a$ reaches a preset value (such as −20 mmHg) in order to prevent overflow of the enclosed space that may dislodge wound interface 15 from skin surface 11. As yet another example, the control group may regulate input of liquid 24 to maintain the actual pressure $p_a$ of liquid 24 in enclosed space 17 at a target pressure $p_0$ (such as −20 mmHg or ambient pressure $p_{amb}$) in order to prevent overflow of the enclosed space that may dislodge wound interface 15 from skin surface 11 when liquid 24 is simultaneously input as input fluid 16 and withdrawn as output fluid 18 from the enclosed space.

Data 73 may be communicated between controller 87 and pressure sensor 91 to control the sensing of pressure by pressure sensor 91, for example, the frequency of pressure sensing. Data 73 may be indicative of pressure as sensed by pressure sensor 91.

Input fluid 16 may be communicated under pressure of gas source 82 (e.g., a tank of compressed gas), pressure of liquid source 84 (e.g., piezometric head at liquid source), suction of pump 89, and combinations thereof. Pump 89 may withdraw output fluid 18 from enclosed space 17. Pump 89 may be, for example, a centrifugal pump, positive displacement pump, or peristaltic pump, in various implementations. Data 72, for example, may be communicated from controller 87 to pump 89 to control a speed of pump 89 or data 72 may be indicative of the actual speed of pump 89 as communicated from pump 89 to controller 87.

Wound therapy apparatus 10 may include various fluid conveyances, for example hoses, pipes, valves, tubing, connectors, pressure regulators, plenums, and various other fittings, to communicate gas 22 and liquid 24 from gas source 82 and liquid source 84, respectively, to enclosed space 17 of wound interface 15 as input fluid 16 and to communicate output fluid 18 withdrawn from enclosed space 17 of wound interface 15. Communication pathways 61, 62, 63, 64 may be, for example, wired, wireless, optical (e.g., fiberoptic, infrared), networked (e.g., Internet), or various combinations thereof, in various implementations. Valve 88, pump 89, and pressure sensor 91 may include, for example, A/D converters, D/A converters, actuators, solenoids, stepper motors, microprocessors, to control the operations of valve 88, pump 89, and pressures sensor 91 using data 71, 72, 73, respectively, or to communicated data 71, 72, 73 to controller 87 indicative of the operation of valve 88, pump 89, and pressure sensor 91, as would be readily recognized by those of ordinary skill in the art upon study of the present disclosure. Data 71, 72, 73, 74 may be digital, analog, or combinations thereof, in various implementations.

One or more power source(s) may be disposed about wound therapy apparatus 10 in electrical communication with controller 87, valve 88, pump 89, and pressure sensor 91 to flow electrical power thereupon. The power source(s) may be, for example, mains electric, battery, or combinations of mains electric and battery, and the power source(s) may include, for example, a transformer, an inverter, a rectifier, filter(s), surge protector, as would be readily recognized by those of ordinary skill in the art upon study of the present disclosure.

Figure 3A:
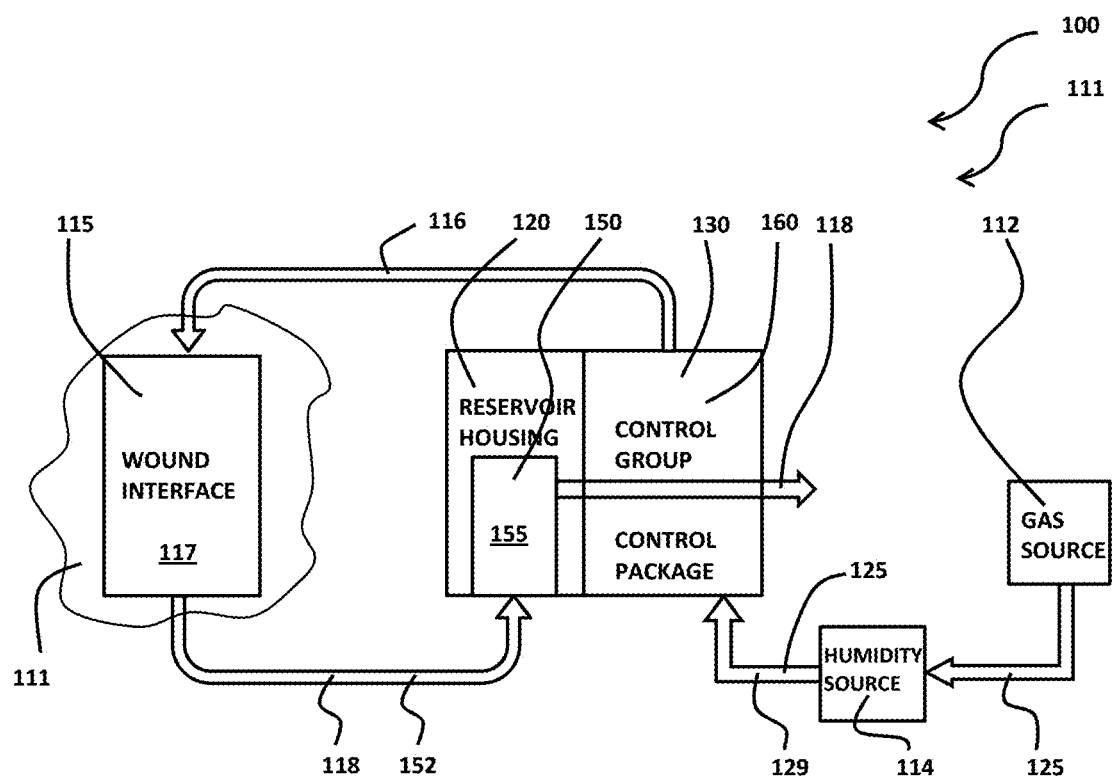
FIG. 3A illustrates by schematic diagram a second exemplary implementation of a wound therapy apparatus in a first operational configuration.
Figure 3B:
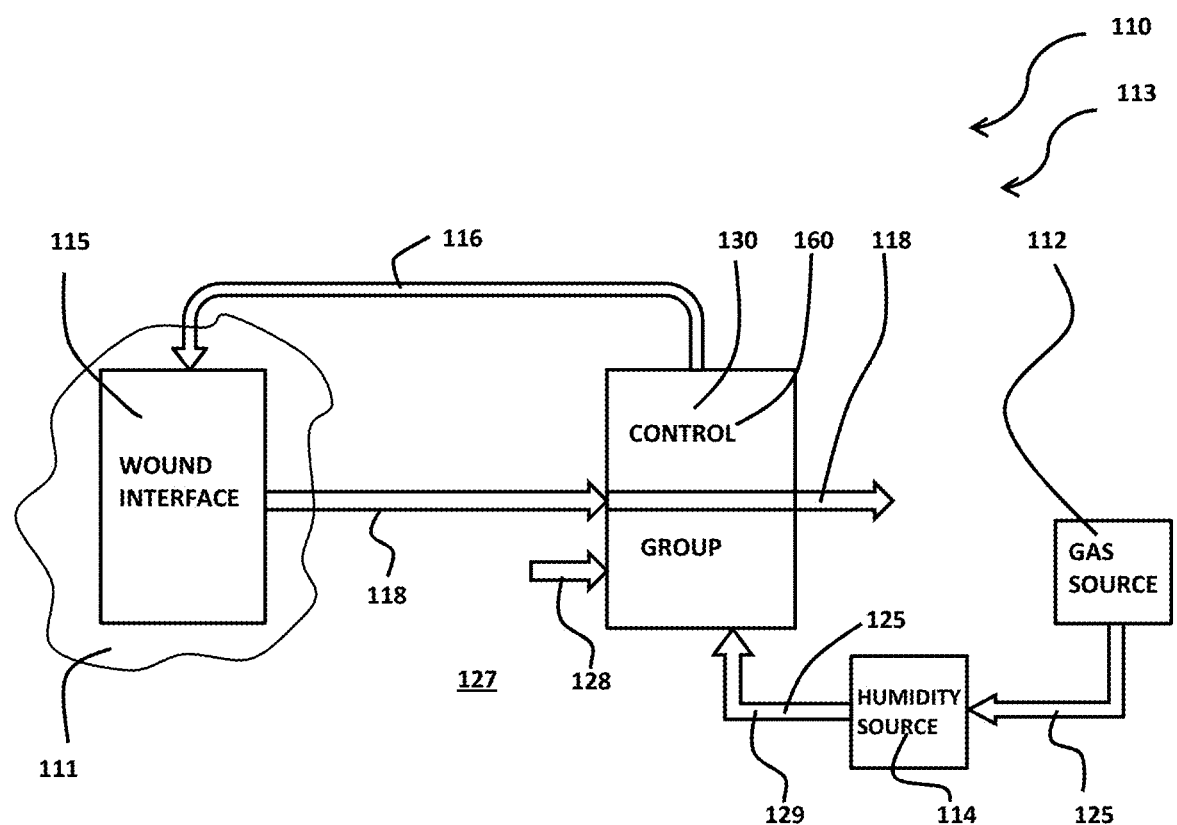
FIG. 3B illustrates by schematic diagram the exemplary implementation of a wound therapy apparatus of FIG. 3A in a second operational configuration.

FIGS. 3A, 4A and FIGS. 3B, 4B illustrate exemplary wound therapy apparatus 100 in operational configurations 111, 113, respectively. In operational configuration 111, as illustrated in FIG. 3A, control group 130, includes reservoir housing 120 and control package 160 releasably secured to one another. As illustrated in FIG. 3B, reservoir housing 120 has been removed from releasable securement to control package 160 so that control group 130 includes only control package 160 in operational configuration 113. Accordingly, in exemplary wound therapy apparatus 100, control group 130 may be operably configured as either reservoir housing 120 in releasable securement to control package 160 per operational configuration 111, or control package 160 alone per operational configuration 113.

As illustrated in FIGS. 3A, 3B, wound therapy apparatus 100 includes gas source 112, humidity source 114, wound interface 115 that defines enclosed space 117, and control group 130. Control package 160 of control group 130 selects input fluid 116 as either gas 125 from gas source 112 plus humidity 129 from humidity source 114 or air 128 from atmosphere 127, and control package 160 controls the input of input fluid 116 into enclosed space 117 of wound interface 115, the withdrawal of output fluid 118 from enclosed space 117 of wound interface 115, and the exhausting of at least portions of output fluid 118 into the atmosphere, as illustrated in FIGS. 3A, 3B. Wound therapy apparatus 100 includes various fluid conveyances, for example hoses, pipes, valves, tubing, connectors, plenum, reservoirs, and various other fittings, to communicate gas 125 from gas source 112 and air 128 from atmosphere 127 into enclosed space 117 as input fluid 116 and to communicate output fluid 118 between wound interface 115 and control group 130. Input fluid 116 as air 128 from atmosphere 127 may be input into the enclosed space 117 to set actual pressure $p_a$ within the enclosed space 117 to ambient pressure $p_{amb}$ in the event of power failure of wound therapy apparatus 100.

As illustrated in FIG. 3A, reservoir housing 120 includes reservoir 150, and output fluid 118 withdrawn from enclosed space 117 passes through reservoir 150. Reservoir 150 captures exudate 152 including other liquids from output fluid 118 in chamber 155 of reservoir 150, in the implementation of FIG. 3A. Gaseous portions of output fluid 118 or gas displaced from chamber 155 of reservoir 150 by capture therein of exudate 152 may then be discharged to the atmosphere 127 from pump 189, as illustrated. Reservoir 150 may be, for example, a canister, container, or space within reservoir housing 120 that may comprise substantially the interior of reservoir housing 120. Reservoir 150 and reservoir housing 120 may be formed as a unitary structure in certain implementations. Reservoir 150 may be removable and replaceable in some implementations. Reservoir 150 may be openable to allow reservoir 150 to be emptied and reused, in some implementations. In other implementations, reservoir 150 is sealed so as not to be reusable. In such implementations, reservoir housing 120 may functionally become the reservoir and may be replaced in its entirety. Accordingly, either reservoir 150, or reservoir housing 120 with or without reservoir 150, may be formed to be disposable. Chamber 155 of reservoir 150 may include a pad layer or pouch of super absorbent polymer to gel exudate 152. Odor neutralizing agents may optionally also be included in reservoir housing 120 including within chamber 155.

As illustrated in FIG. 3B, reservoir housing 120 has been removed from releasable securement to control package 160 and control group 130 includes only control package 160 in operational configuration 113. Input fluid 116 flows under the control of control package 160 to wound interface 115, and output fluid 118 flows from wound interface 115 towards control package 160 without passage through reservoir housing 120 in operational configuration 113, as illustrated in FIG. 2B. Reservoir housing 120 may be disengaged from control package 160 placing control group 130 in operational configuration 113 because, for example, exudate 152 from the wound bed is low to non-existent, wound interface 115 retains exudate 152 within wound interface 115, or it is desirable for the patient to be unencumbered by reservoir housing 120. Control group 130 may recognize the change in configuration and deliver therapies that are appropriate for the applicable corresponding configuration.

Figure 4A:
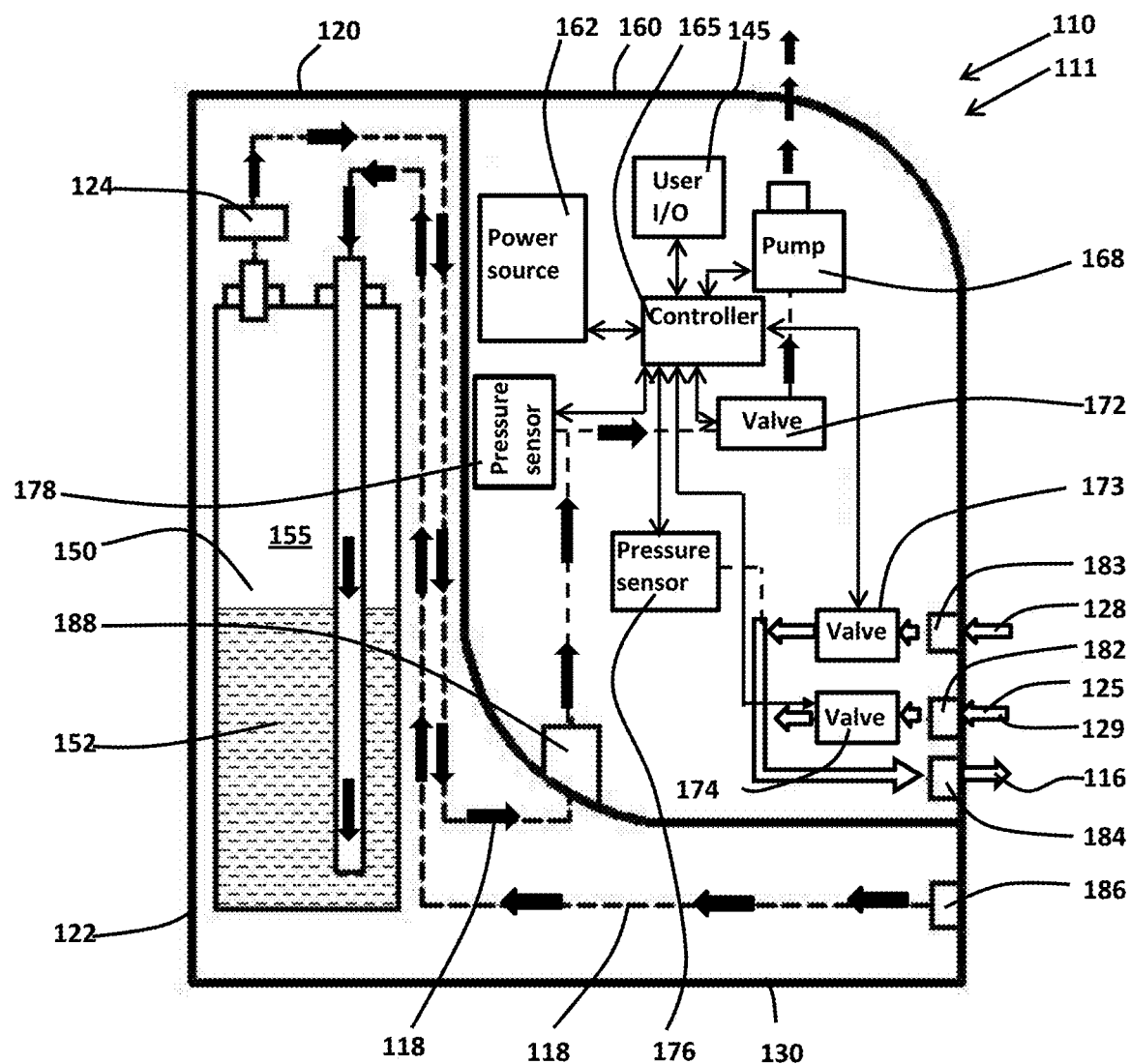
FIG. 4A illustrates by cut-away schematic diagram a portion of the exemplary wound therapy apparatus of FIG. 3A in the first operational configuration.

As illustrated in FIG. 4A, control package 160, includes power source 162 that may variously be, for example, a battery, mains electric, or a battery in combination with mains electric with the battery providing back-up power. Power source 162, in various implementations, may include, for example, a transformer, inverter, and regulatory circuitry, as would be readily understood by those of ordinary skill in the art upon study of this disclosure. If power source 162 includes a battery, the battery may be, for example, nickel cadmium, nickel metal hydride, or lithium ion based.

Power source 162 is in electrical communication with various components of controller 60 including controller 165, pump 168, valves 172, 173, 174, pressure sensor 176, pressure sensor 178, and user I/O 145 to flow power thereto, in this implementation. Various electrical pathways may be disposed about control group 130 to communicate electrical power from power source 162 to controller 165, pump 168, valves 172, 173, 174, pressure sensors 176, 178, and user I/O 145. Pump 168 may be, for example, a rotary pump or a positive displacement pump, in various implementations. Valves 172, 173, 174 may be electromechanically actuated by, for example, solenoid or stepper motor. One or more of the valves 172, 173, 174 may be configured as a three-way valve or as a combination of valves, in various implementations. While this implementation includes pressure sensors 176, 178, other implementations may include a single pressure sensor that functions as the combined pressure sensors 176, 178 or senses pressures of different locations. Other implementations of control group 130 may include various numbers of valves, such as valves 172, 173, 174 that work in conjunction with various numbers of pressure sensors, such as pressure sensors 176, 178, to measure and regulate the pressure(s), leading up to, within, or downstream from, a compartment or housing. Such multi-point sensing may enable a more intelligent differential monitoring and diagnosis of a system or fault condition and may pin point the location and nature of a condition to facilitate troubleshooting, adjustment, or corrective action.

Controller 165 controls, at least in part, the operation of wound therapy apparatus 10 including control group 130, in this implementation. Controller 165 may include, for example, a microprocessor, memory, A/D converter, D/A converter, clock, I/O connectors, and so forth, as would be readily recognized by those of ordinary skill in the art upon study of this disclosure. Controller 165 may communicate with power source 162 to monitor power source 162, to receive power from power source 162, or to regulate the flow of power from power source onto pump 168, valves 172, 173, 174, pressure sensors 176, 178, and user I/O 145. Controller 165 may communicate operatively with pump 168, valves 172, 173, 174, pressure sensors 176, 178 to regulate the operation thereof. Controller 165 may communicate operatively with pump 168, valve 172, valve 174, pressure sensors 176, 178 to receive information from pump 168, valves 172, 173, 174, pressure sensors 176, 178 indicative of the operation thereof or indicative of the operation of wound therapy apparatus 100.

User I/O 145, which may be placed exteriorly about control group 130 or remotely from control group 130, may include a display for the display of the operational status of wound therapy apparatus 100 to a user. User I/O 145 may include various switches, push buttons, dials, and so forth, whether virtual or physical for obtaining user inputs to allow the user to regulate the operation of wound therapy apparatus 100 including control group 130. User I/O 145 and controller 165 may communicate with one another to communicate user inputs from user I/O 145 to controller 165 to regulate the operation of wound therapy apparatus 100 including control group 130 and to communicate information from controller 165 to user I/O 145 indicative of operations of wound therapy apparatus 100.

Various communication pathways such as wired, optical (e.g. LASER, IR), and network may be included about wound therapy apparatus 10 including control group 130 for communication between controller 65 and pump 68, valve 72, valve 73, valve 74, pressure sensors 76, 78, and user I/O 45. For example, in some implementations, at least portions of user I/O 145 may be remote from the remainder of control group 130, such as on a smart phone application, and user I/O 145 may communicate with controller 165 by various networks that may be wireless, at least in part. User I/O 145 may interface with a network such as the Internet by wired or wireless connection to communicate data indicative of operations of wound therapy apparatus 100 via networked communication or to receive inputs that regulate operations of wound therapy apparatus 100.

As illustrated in FIG. 3B, control group 130 includes control package 160, and control package 160 includes power source 162, controller 165, pump 168, valves 172, 173, 174 pressure sensors 176, 178, and user I/O 145. Reservoir housing 120 has been removed from engagement with control package 160, in operational configuration 113, so that control group 130 includes control package 160 and excludes reservoir housing 120, as illustrated in FIG. 3B.

Wound therapy apparatus 100 may be placed in operational configuration 111, as illustrated in FIG. 3A. As illustrated in FIG. 3A, wound interface 15 is secured to a skin surface 111 to enclose a wound bed, such as wound bed 113, 213, 313, within enclosed space 117 that is fluid tight. Wound interface 15, control group 130 including both reservoir housing 120 and control package 160, humidity source 114, and gas source 112 are then placed in fluid communication with one another, as indicated in FIG. 3A. Wound therapy apparatus may be placed in operational configuration 111 when the wound bed is exuding exudate 152, for example, in early stages of wound therapy, because operational configuration 111, as illustrated in FIGS. 3A, 4A, includes reservoir 150 for the collection of exudate 152.

Figure 4B:
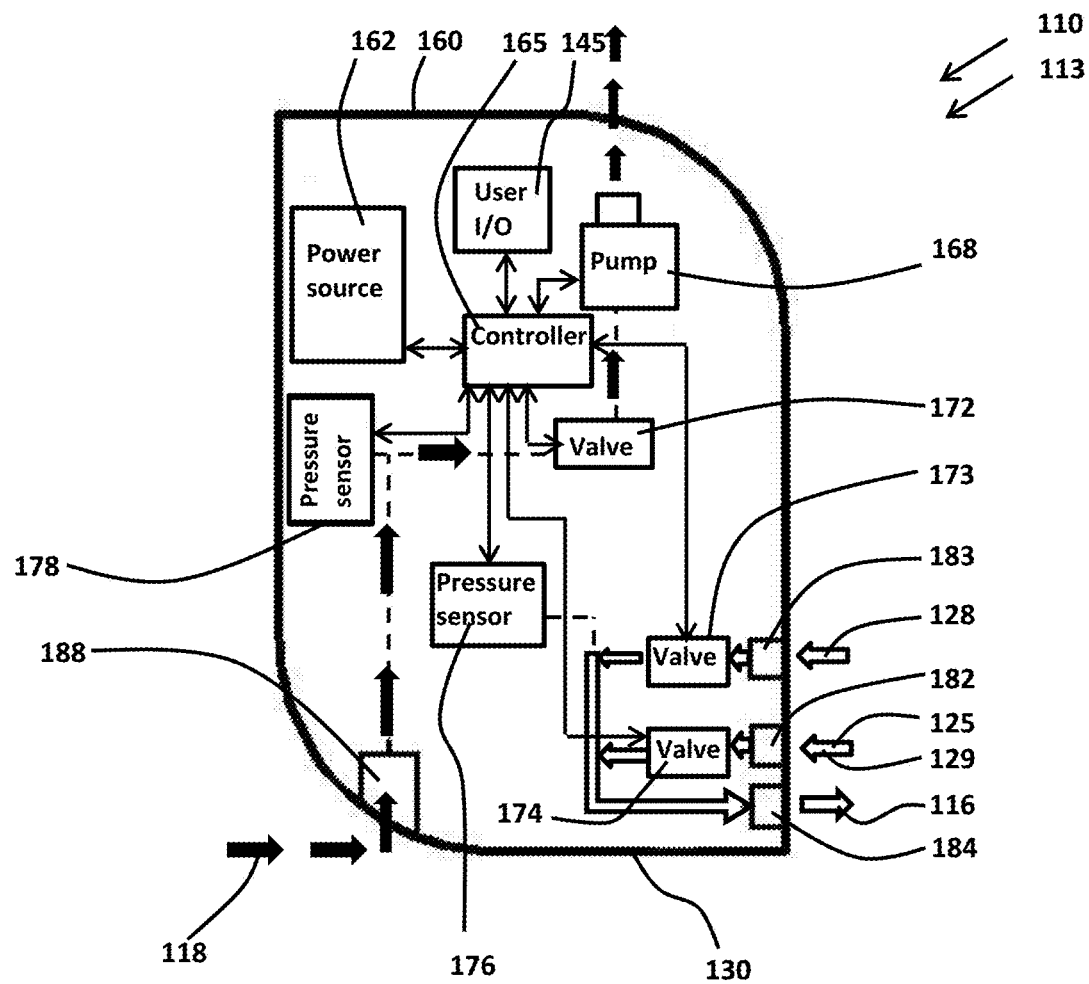
FIG. 4B illustrates by cut-away schematic diagram a portion of the exemplary wound therapy apparatus of FIG. 3A in the second operational configuration.

As illustrated in FIGS. 4A, 4B, gas 125 from gas source 112 combined with humidity 129 from humidity source 114 is in communication with valve 174 through connector 182 of control group 130, and air 128 from atmosphere 127 is in communication with valve 173 through port 183 of control package 160. Note that, in FIGS. 4A, 4B, the path of input fluid 116 is indicated by arrows having a white interior, and the path of output fluid 118 is indicated by solid black arrows. Input fluid 116 may be selected as either air 128 or gas 125 including humidity 129 or by operation of valves 173, 174. Controller 165 may operate valve 174 to select gas 125 plus humidity 129 as input fluid 116, or controller 165 may operate valve 173 to select air 128 as input fluid. Input fluid 116 then flows either from valve 173 or from valve 174, through connector 184 of control group 130, and thence into the enclosed space 117 of the wound interface 115.

Note that some implementations may omit humidity source 114, for example, when the flow rate of input fluid 116 is low the oxygen flow is very low and, thus, humidification is not required as moisture in the wound bed is sufficient. Also, it should be recognized that gas source 112 may include multiple gas sources that may supply a variety of gasses and combinations of gasses as gas 125, and the composition of gas 125 may vary during the course of wound therapy. The user may variously select the composition of gas 125 for use during various times of wound therapy.

As illustrated in FIG. 4A, pressure sensor 176 is in operable communication with enclosed space 117 including input fluid 116 as input fluid 116 is being input into enclosed space 117 to detect the actual pressure $p_a$ within the enclosed space 117, in this implementation. The actual pressure $p_a$ within enclosed space 117 as detected by pressure sensor 176 is communicated from pressure sensor 176 to controller 165, and controller 165 may position either valve 173 or valve 174 to regulate flow of input fluid 116 into the enclosed space 117 in order to cause actual pressure $p_a$ to proximate the target pressure $p_0$ within the enclosed space 117 (i.e., make $p_a \approx p_0$), in this implementation.

Pressure sensor 178 is in operable communication with enclosed space 117 including output fluid 116 as output fluid 118 is being withdrawn from enclosed space 117 to detect the actual pressure $p_a$ within the enclosed space 117, in this implementation. The actual pressure $p_a$ within the enclosed space as detected by pressure sensor 178 may be communicated from pressure sensor 178 to controller 165, and controller 165 may position valve 172, regulate pump 168, or both position valve 172 and regulate pump 168 in order to regulate flow 118 from the enclosed space, and, thus, cause actual pressure $p_a$ to proximate the target pressure $p_0$ within the enclosed space 117 (i.e., make $p_a \approx p_0$).

As illustrated in FIG. 4A, output fluid 118, withdrawn, at least in part, by pump 168, flows from the enclosed space of wound interface 115 through connector 186 of control group 130, through reservoir 150, towards filter 124, towards connector 188 between reservoir housing 120 and control package 160, towards pump 168 under the control of valve 172. Exudate 152 including other liquids is retained in chamber 155 as output fluid 118 flows through chamber 155 of reservoir 150, and exudate 152 including other liquids may also be captured by filter 124 as output fluid 118 as output fluid 118 passes through filter 124, as illustrated. The remaining gaseous portions of output fluid 118 are then exhausted into the atmosphere on the discharge side of pump 168, as illustrated.

Filter 124 prevents exudate 152 including other liquid in output fluid 118 from reaching control package 160 including pump 168, thereby serving a protective function. For example, in some implementations, filter 124 may include a hydrophobic ultra-high molecular weight polyethylene (UHMW-PE) that may optionally be impregnated with carboxymethyl cellulose. Filter 124 may include a hydrophobic filter material may comprise of sintered PTFE with optional addition of a super absorbent polymer such as sodium polyacrylate, or sodium carboxymethyl cellulose. When exudate 152 reaches filter 124, filter 124 clogs and expands abruptly, for example, increasing the pressure detected by pressure sensor 178, that, in turn, may trigger a protective shutoff of pump 168 by controller 165. Filter 124 may be replaceably received within reservoir housing 120, or filter 124 may be omitted, in various implementations.

Note that various numbers and combinations of valve(s), such as valves 172, 173, 174, and pressure sensor(s), such as pressure sensors 176, 178, may be used in combination with controller 165 to regulate the flow of input fluid 116 into the enclosed space 117 or to regulate the flow of output fluid 118 from the enclosed space 117 in order to cause actual pressure $p_a$ to proximate target pressure $p_O$ within the enclosed space. For example, valves 173 174 may be replaced with a three-way valve that selectable between no flow, flow of air 182, or flow of gas 125 including humidity 129.

Alternatively, in operation, wound therapy apparatus 100 may be placed in operational configuration 113, as illustrated in FIGS. 3B, 4B. As illustrated, wound interface 115 is secured to skin surface 111 to enclose a wound bed, such as wound bed 213, 313, 413, within enclosed space 117 that is fluid tight. Wound therapy apparatus 100 may be placed in operational configuration 113, as illustrated in FIGS. 3B, 4B when the wound bed is no-longer exuding exudate 152, for example, in later stages of healing of the wound bed. Operational configuration 113 excludes reservoir 150 including reservoir housing 120 from control group 130, as reservoir 150 including reservoir housing 120 may not be needed, in this implementation. Filter 124 may be included in controller group 130 in operational configuration 113 to capture stray liquids, in certain implementations.

As illustrated in FIG. 4B, output fluid 118, propelled, at least in part, by pump 168, flows from the enclosed space 117 of wound interface 115 through connector 188 of control package 160 of control group 130, through valve 172, and through pump 168. Output fluid 118 is then exhausted into the atmosphere on the discharge side of pump 168, in this implementation. Input fluid 116 may flow from either gas source 112 or atmosphere 127 to the enclosed space of wound interface 115 in operational configuration 113 as described with respect to operational configuration 111 illustrated in FIGS. 3A, 4A. In operational configuration 113, controller 165 interacts with valves 172, 173, 174, pressure sensors 176, 178, and pump 168 to control the flow of input fluid 116 and output fluid 118, for example, in order to cause actual pressure $p_a$ to proximate target pressure $p_O$ within the enclosed space or to deliver air 128 to the wound bed.

Connector 188 forms a point of attachment between reservoir housing 120 and control package 160 so that reservoir housing 120 and control package 160 are removably secured to one another at least at connector 188 in operational configuration 111. Connector 188 forms a fluid pathway for flow of output fluid 118 from reservoir housing 120 to control package 160 when reservoir housing 120 and control package 160 are removably secured to one another in operational configuration 111. Reservoir housing 120 is absent from control group 130 in operational configuration 113, and connector 188 provides a point for attachment of fluid conveyances between wound interface 115 and control package 160 to convey output fluid 118, in operational configuration 113. Connectors 182, 184, 186 provide points of attachment for various fluid conveyances to control group 130 that allow input fluid 116 and output fluid 118 to flow therethrough, in this implementation.

Reservoir housing 120 may be removed from securement to control package 160 by disconnection at least at connector 188, and a new reservoir housing 120 may be removably secured to control package 160 at least by securement at connector 188, in this implementation. Alternatively, reservoir housing 120 may be removed from securement to control package 160 by disconnection of at least at connector 188, and fluid conveyances between wound interface 115 and control package 160 may be secured to connector 188 thereby placing wound therapy apparatus 100 from operation configuration 111 into operational configuration 113, in this implementation.

Figure 5:
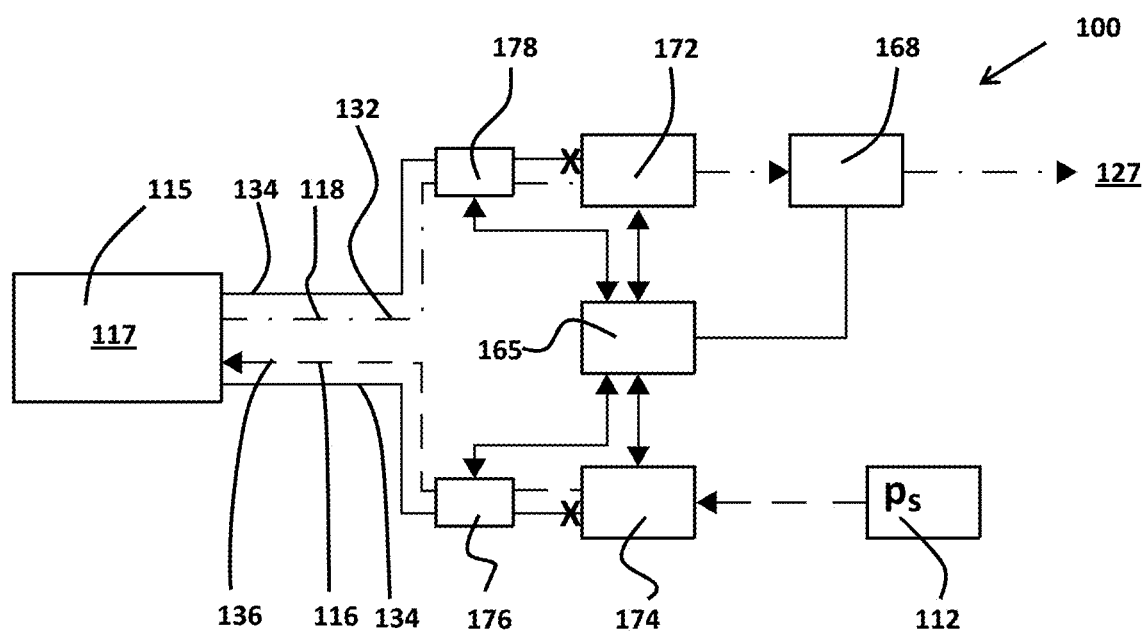
FIG. 5 by schematic diagram operational states of the exemplary wound therapy apparatus of FIG. 3A.

As illustrated in FIG. 5, controller 165 is in operable communication with valves 172, 174, pressure sensors 176, 178, and pump 168 to vary actual pressure $p_a$ within enclosed space 117 generally over the pressure range $p_{min} \leq p_a \leq p_{max}$ in correspondence to target pressure $p_O$ that may vary periodically within the pressure range $p_{min} \leq p_O \leq p_{max}$ where $p_{min}$ is the minimum value of target pressure $p_O$ and $p_{max}$ is the maximum value of target pressure $p_O$.

In various implementations, $p_{min} \leq p_{amb}$ where $p_{amb}$ is the ambient pressure of atmosphere 127 proximate wound therapy apparatus 100. In various implementations, $p_{max} \geq p_{amb}$. In certain implementations, $p_{max} \leq p_{amb}$. The minimum pressure may be, for example, $p_{min} \approx p_{amb} - 130$ mm Hg. The minimum pressure may be, for example, $p_{min} \approx p_{amb} - 90$ mm Hg. The minimum pressure $p_{min}$ may be, for example, within the pressure range $(p_{amb} - 130 \text{ mm Hg}) \leq p_{min} < p_{amb} - 90$ mm Hg). The minimum pressure $p_{min}$ may be generally within the pressure range $(p_{amb} - 90 \text{ mm Hg}) \leq p_{min} < p_{amb}$. In various implementations, the periodic variation of the target pressure $p_O$ may be generally within the pressure range $p_{min} \leq p_O \leq p_{max}$ where $p_{max} > p_{amb}$. For example, $p_{max} \approx (p_{amb} + 40 \text{ mm Hg})$. In some implementations, the maximum pressure $p_{max}$ may be slightly less than ambient pressure $p_{amb}$, for example, generally within the range of $p_{amb} - 5$ mm Hg to $p_{amb} - 20$ mm Hg.

FIG. 5 illustrates exemplary operational states 132, 134, 136 of wound therapy apparatus 100 as target pressure $p_O$ is varied periodically within the pressure range $p_{min} \leq p_O \leq p_{max}$, and wound therapy apparatus 100 may be varied between operational states 132, 134, 136 to cause the actual pressure $p_a$ to correspond to target pressure $p_O$. Operational states 132, 134, 136 are exemplary, not limiting, so that wound therapy apparatus 100 may be placed in operational states other than operational states 132, 134, 136. Note that wound therapy apparatus varies sequentially between operational states 132, 134, 136 so that, for example, operational states 132, 136 do not exist simultaneously. FIG. 5 excludes humidity source 114, and reservoir 150 for clarity of explanation, so that FIG. 5 is illustrative of the operation of wound therapy apparatus 100 in both operational configurations 111, 113. Valve 173, which is also omitted from FIG. 5 for clarity of explanation, is in the CLOSED position in exemplary operational states 132, 134, 136 illustrated in FIG. 5.

In exemplary operational state 132, as illustrated in FIG. 5 (indicated by dot-dash line in FIG. 5), output fluid 118 is being withdrawn from enclosed space 117 of wound interface 115 to vary the actual pressure $p_a$ in correspondence with target pressure $p_0$ toward minimum pressure $p_{min}$ in order to achieve $p_a \approx p_0 = p_{min}$, or to remove exudate 152 from the enclosed space 117. Pump 168 may be in an ON condition in operational state 132. Output fluid 118 flows from enclosed space of wound interface 115 through valve 172, which is in an OPEN position, propelled by pump 168, and gaseous portions of output fluid 118 are discharged into the atmosphere 127 by pump 168, as illustrated. Valve 174 is in a CLOSED position, so that no input fluid 116 is being input into enclosed space of wound interface 115 in operational state 132, as illustrated. Pressure sensor 178 is in operative communication with the enclosed space of wound interface 115 to detect actual pressure $p_a$ within the enclosed space 117 including output fluid 118, in this implementation. The actual pressure $p_a$ detected by pressure sensor 178 may be communicated from pressure sensor 178 to controller 165, and controller 165 may position valve 172 between OPEN position and CLOSED position including positions intermediate of OPEN position and CLOSED position to achieve $p_a \approx p_0$ as target pressure $p_0$ is decreased toward $p_{min}$. Controller 165 may adjust operations of pump 168 including, for example, the speed of pump 168 in order to achieve $p_a \approx p_0$ and to achieve $p_a \approx p_0 \approx p_{min}$.

In exemplary operational state 134, as illustrated in FIG. 5 (indicated by solid line in FIG. 5), valves 172, 174 are both in CLOSED position, so there is generally no input of input fluid 116 into enclosed space 117 or withdrawal of output fluid 118 out of enclosed space 117. For example, either $p_a \approx p_0 \approx p_{min}$ or $p_a \approx p_0 \approx p_{max}$ in the enclosed space 117 of wound interface 115, in operational stage 134.

While in general there is no input of input fluid 116 into enclosed space 117 of wound interface 115 and no withdrawal of output fluid 118 out of enclosed space 117 at operational stage 134, it should be recognized that there may be some leakage into or out of enclosed space 117 of wound interface 115. Accordingly, at operational state 134, pressure sensor 176, pressure sensor 178, or both pressure sensors 176, 178 may detect actual pressure $p_a$ within enclosed space of wound interface 115, and the actual pressure $p_a$ detected by pressure sensor 176, 178 may be communicated from pressure sensor 176, 178 to controller 165. Controller 165 may position valves 172, 174, alter pump 168 between the OFF state and the ON state, or adjust the operation of pump 168 or valves 172, 174 intermittently, for example, in order to maintain $p_a \approx p_0 \approx p_{min}$, to maintain $p_a \approx p_0 \approx p_{max}$, or to withdraw exudate 152 from the enclosed space 117 of wound interface 115 as needed, in exemplary operational stage 134.

Figure 7:
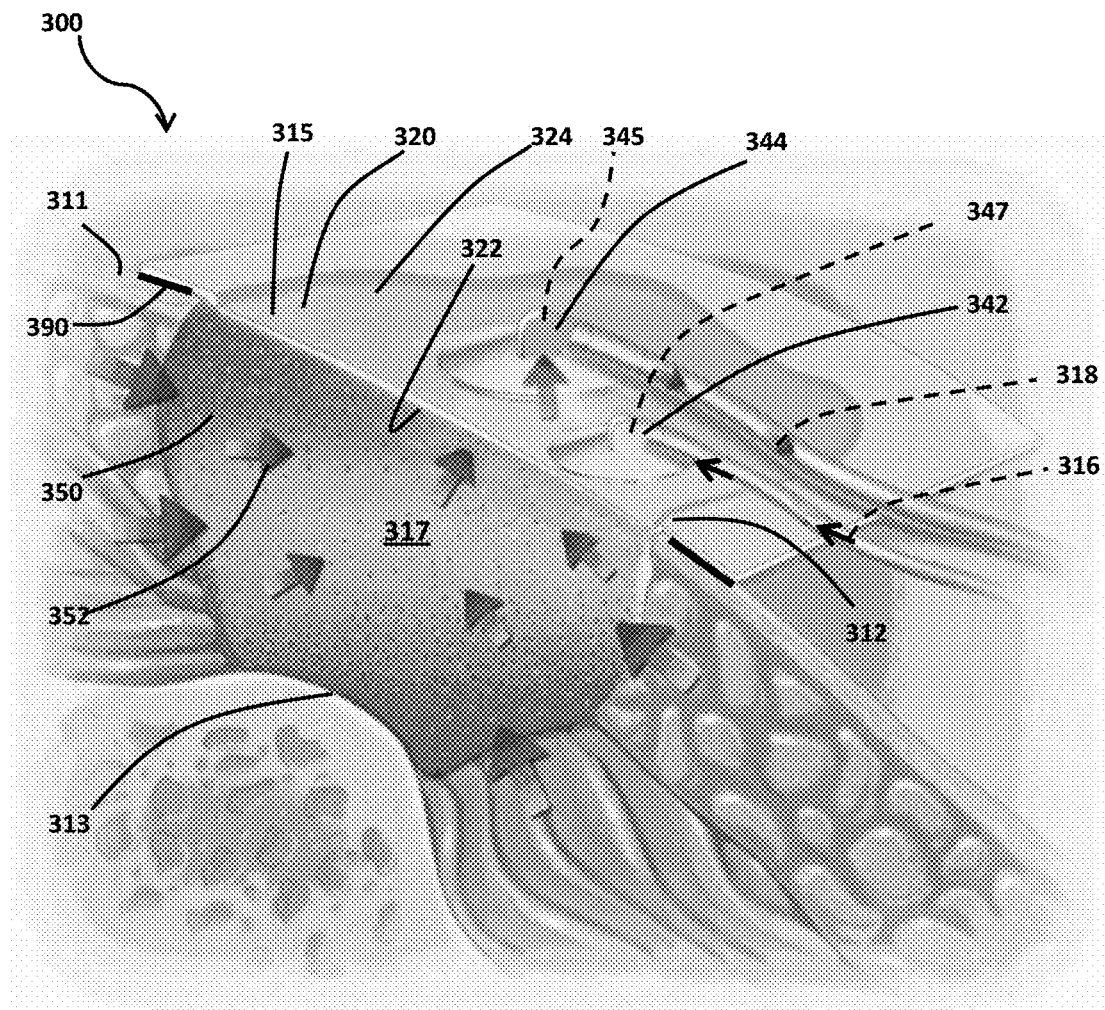
FIG. 7 illustrates by cut-away perspective view a fourth exemplary implementation of a wound interface.

In exemplary operational state 136, as illustrated in FIG. 7 (indicated by dashed line), input fluid 116 is being input into enclosed space 117 of wound interface 115 to vary the actual pressure $p_a$ in correspondence with the target pressure $p_0$ toward maximum pressure $p_{max}$ in order to achieve $p_a \approx p_0 \approx p_{max}$. Input fluid 116 flows into enclosed space 117 of wound interface 115 through valve 174, which is in OPEN position, and the flow of input fluid 116 into the enclosed space 117 is driven by pressure $p_s$ at gas source 112, in this implementation. Valve 172 is in CLOSED position, so that there is no output fluid 118 being withdrawn from enclosed space 117 of wound interface 115 while input fluid 116 is being input into enclosed space 117 in operational state 136. Pressure sensor 176 is in operative communication with the enclosed space 117 of wound interface 115 including input fluid 116 to detect actual pressure $p_a$ within the enclosed space 117 of wound interface 115 at operational state 136, in this implementation. The actual pressure $p_a$ detected by pressure sensor 176 may be communicated from pressure sensor 176 to controller 165, and controller 165 may position valve 174 between OPEN position and CLOSED position including positions intermediate of OPEN position and CLOSED position in order to achieve $p_a \approx p_0$ as target pressure $p_0$ is increased toward $p_{max}$. Pump 168 may be in an OFF condition in operational state 136.

Thus, as illustrated in FIG. 5, valves 172, 174 are positioned between the OPEN position and the CLOSED position to sequentially input the input fluid 116 into enclosed space 117 and withdraw output fluid 118 from the enclosed space 117, meaning that withdrawal of output fluid 118 and the input of input fluid 116 does not occur simultaneously. Input fluid 116 may be being input into the enclosed space or output fluid 118 may be being withdrawn from the enclosed space but not the input of input fluid 116 simultaneously with output of output fluid 118, in this illustrated implementation. Thus, valve 172 may be in the OPEN position simultaneously with valve 174 in the CLOSED position, valve 172 may be in the CLOSED position simultaneously with valve 174 in the OPEN position, or valve 172 may be in the CLOSED position simultaneously with valve 174 in the CLOSED position, but valves 172, 174 are never both in the OPEN position at the same time, in this illustrated implementation.

Pressure sensor 176 or other pressure sensor(s) disposed about control group 130 may, for example, detect that pressure $p_s$ at gas source 112 is below some minimum value indicating that gas source 112 is exhausted. As another example, control group 130 may be disconnected from gas source 112. Valve 174 may then be placed in the CLOSED position, and valve 173 may be altered between CLOSED position and OPEN position in lieu of valve 174 in order to alter wound therapy apparatus between operational states 132, 134, 136. Air 128 from atmosphere 127 as regulated by valve 173 is then input into enclosed space 117, for example to vary the actual pressure $p_a$ in correspondence with the target pressure $p_0$ toward maximum pressure $p_{max}$.

Figure 6A:
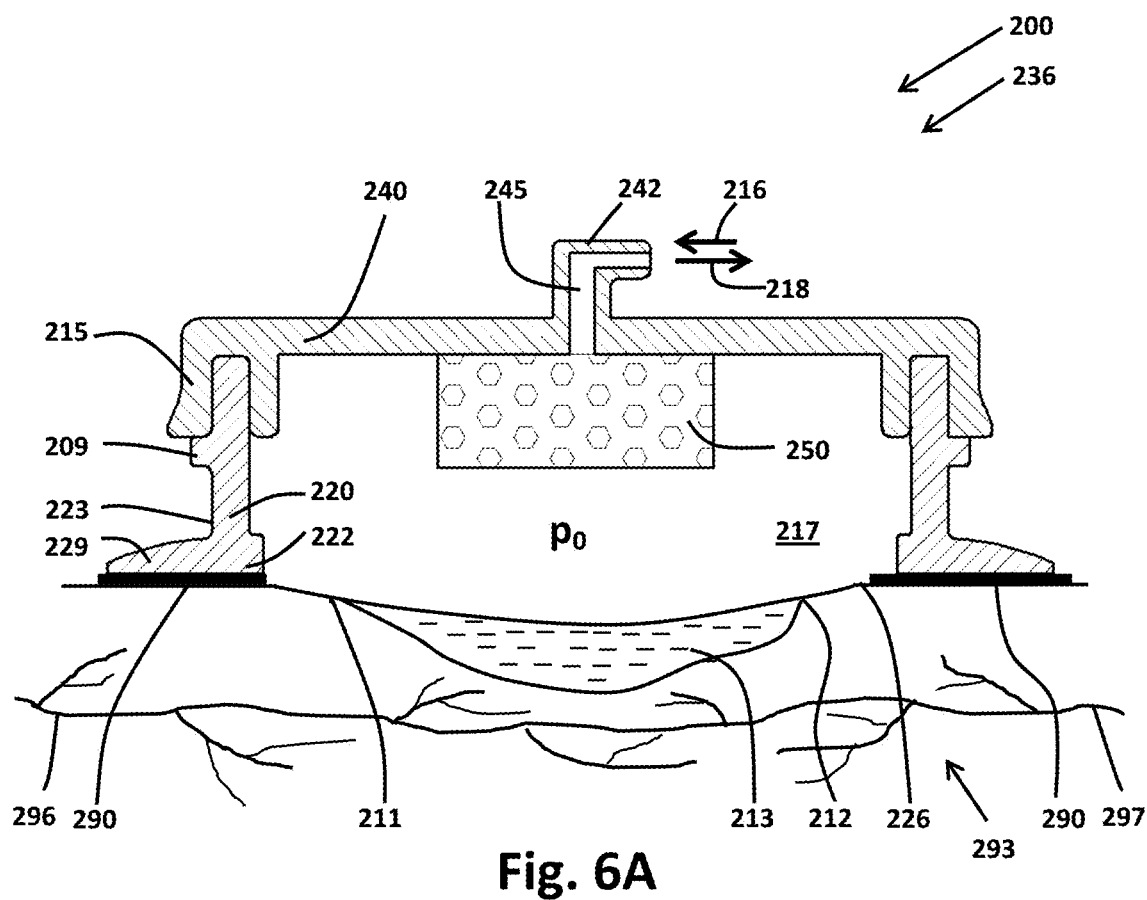
FIG. 6A illustrates by cut-away elevation view a third exemplary implementation of a wound therapy apparatus at a first stage of operation.
Figure 6B:
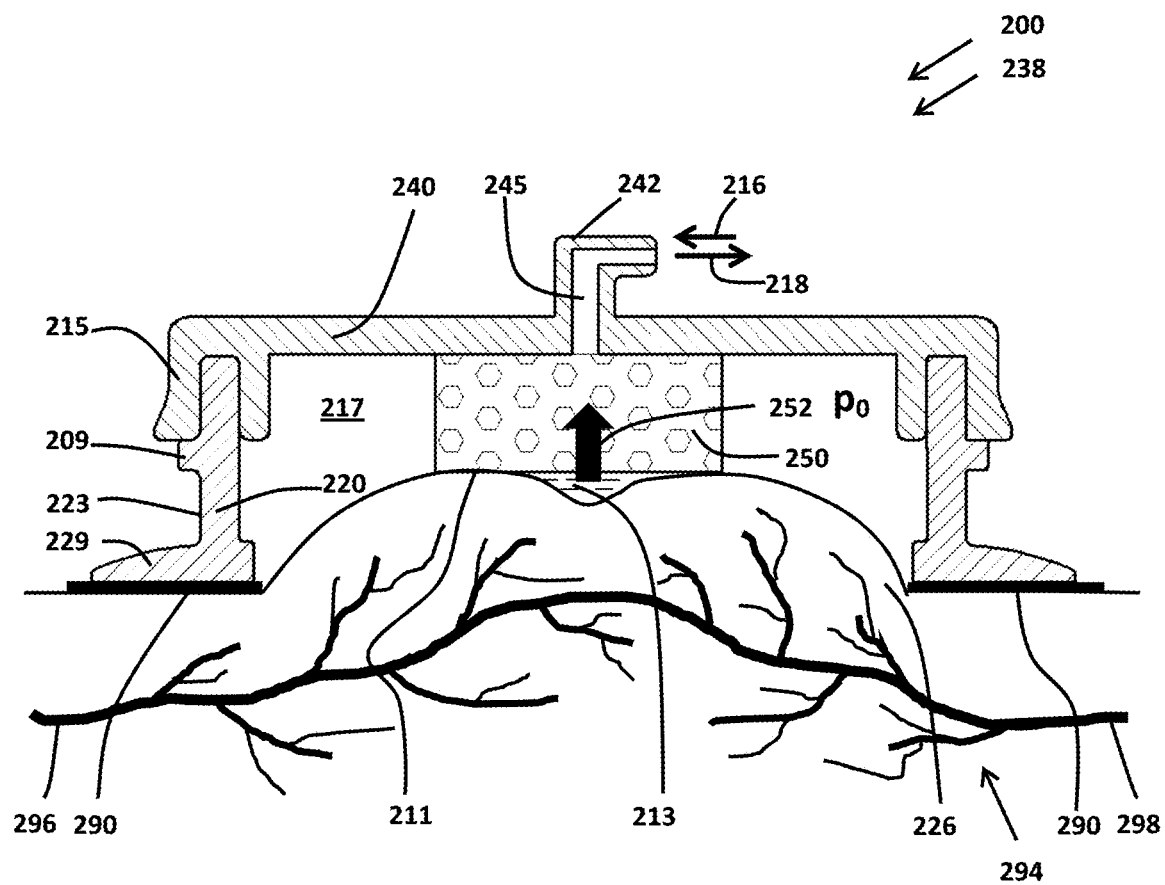
FIG. 6B illustrates by cut-away elevation view portions of the exemplary wound interface of FIG. 6A at a second stage of operation.

FIGS. 6A and 6B illustrate wound therapy apparatus 200 at exemplary first stage of operation 236 and at exemplary second stage of operation 238, respectively. As illustrated in FIGS. 6A, 6B, wound therapy apparatus 200 includes wound interface 215 that is deformation resistant and defines enclosed space 217 that is fluid-tight to enclose wound bed 213 at skin surface 211 when wound interface 215 is engaged with skin surface 211. Wound interface 215, as illustrated, includes cover 240 slidably sealingly frictionally removably engaged with base 220. Cover 240 may include at least transparent portions to allow visual inspection of wound bed 213 though cover 240. Base 220 may include flange 209 around at least portions of an outer perimeter of base 220 that may provide structural support or sealing surface against cover 240, as illustrated.

In other implementations, cover 240 and base 220 may be formed as a unitary structure or cover 240 may be engaged hingedly or engaged in other ways with base 220. While wound interface 215 is illustrated as cylindrical in shape enclosing a circular region of skin surface 211, it should be understood the structure, such as wound interface 215, may assume other geometric shapes to enclose other geometrically shaped regions of skin 211 such as rectangular, polygonal, or ovoid, to enclose various shaped wounds, and may include other modifications such as to base 220 to fit skin surface 211 in various regions of the body, in various other implementations. In other implementations, one or more additional ports in communication with enclosed space 217 may be situated about the wound interface 215 for monitoring parameters within enclosed space 217, communication of fluids with enclosed space 217, or other therapeutic interventions with enclosed space 217.

Base 220, in this implementation, includes flange 229 around the entire perimeter of outer side 223 of base 220 generally at distal end 222 of base 220. Flange 229 is secured to skin surface 211 by adhesive 290, as illustrated in FIGS. 6A, 6B, around the entire perimeter of base 220 to form fluid-tight enclosed space 217, and wound boundary 212 is enclosed within enclosed space 217. Flange 229 may be designed by thickness and/or polymeric material to be soft and conformable to enable sealing of wound interface 215 over a wound 213 in a fluid-tight manner while distributing forces on wound interface 215 from actual pressure $p_a$ within enclosed space 217 over the skin surface 211.

Adhesive layer 290 may optionally extend over portions of skin surface 211 to include all skin surface under and proximate to flange 229 at distal end 222. When the adhesive is a medically suitable member of the cyanoacrylate class, such as N-butyl-2-cyanoacrylate (Histoacryl Blue), or octyl-2-cyanoacrylate (Dermabond), the layer of water-resistant adhesive coating over the peri-wound skin surface serves the additional function of protecting the normal skin from maceration, secondary to prolonged exposure to other fluids, such as exudate, proteolytic enzyme soaks or saline lavages, etc. Other medical adhesives, for example, acrylic, silicone and hydrocolloid may be used to secure flange 229 of wound interface 215 to the skin surface 211. Other securements such as straps with hook-and-loop-type fasteners or cohesive bandages may also be employed in various other implementations to secure, at least in part, wound interface 215 to the skin surface 211. Base 220 of wound interface 215 may be formed of any of various medical polymers including, for example, polycarbonate, polystyrene, polypropylene or ABS; and may further be associated with additional sealing structures such as an inflatably adjustable circumferential cushion between the base and the adhesive layer around the perimeter of the wound bed.

Port 242, which is located about wound interface 215, is in fluid communication with enclosed space 217 via lumen 245, in this implementation. Lumen 245 of port 242 may be in fluid communication with a control group, such as control group 30, 130 of wound therapy apparatus 10, 100, respectively, and the control group may control the input of input fluid 216 into enclosed space 217 or the withdrawal of output fluid 218 from enclosed space 217 via lumen 245, in this implementation.

Input fluid 216 may be input into enclosed space 217 via lumen 245 of port 242, as indicated by the arrow in FIGS. 6A, 6B, for example, to regulate, at least in part, the actual pressure $p_a$ within enclosed space 217, to control the composition of the gaseous fluids within enclosed space 217, or for various therapeutic purposes. Input fluid 216, for example, may be input into enclosed space 217 to increase the actual pressure $p_a$ within enclosed space 217 in conformance to increases in the target pressure $p_0$. Input fluid 216 may include gas, such as gas 22, 125, gas 22, 125 plus humidity 129 from a humidity source, such as humidity source 114. Input fluid may include liquid, such as liquid 24.

Output fluid 218 may include input fluid 216 and output fluid 218 may include exudate 252, so that output fluid 218 may include liquid, gas, and combinations of liquid and gas from within enclosed space 217. Input fluid 216 or output fluid 218 may include liquid, such as liquid 24, that may have various therapeutic purposes. Output fluid 218 is withdrawn from enclosed space 217 through lumen 245 of port 242, as illustrated, for example, to decrease the actual pressure $p_a$ within enclosed space 217 in conformance to decreases in the target pressure $p_0$, to remove exudate 252 from enclosed space 217, or to remove liquid, such as liquid 24, from enclosed space 217.

A pad 250 may be deployed within enclosed space 217 to absorb and transfer exudate 252 away from wound bed 213, and the pad 250 may be in fluid communication with port 242 to allow withdrawal of exudate 252 from wound bed 213 through the pad 250 and thence through port 242. Pad 250 may be formed of materials with absorbent and fluid transfer properties so as to absorb exudate. These materials include, for example, open-cell foam composed, for example, of polyvinyl alcohol (PVA), polyurethane or other polymer foam. Pad 250 may be formed of various woven or non-woven fibers such as sodium carboxymethyl cellulose hydrofiber (Aquacel), or knitted fibers with hydrophobic polyester fiber predominant on outer surface and hydrophilic nylon fibers predominantly on the inside to serve as a conduit to fluid transfer. The hydrophobic polyester fiber wicks away liquid and prevents moisture buildup and secondary maceration of tissue with which pad 250 is in sustained contact. Depending on specific fluid management goal, whether to primarily transfer exudate to another location or primarily to absorb and fix the exudate locally, certain amounts of a super absorbent polymer (SAP), such as sodium polyacrylate, can optionally be included in pad 250. A quantity of SAP is added to a closed-cell polyurethane may enable passage of liquid through the resulting matrix, thereby enhancing the absorbent and fluid transfer properties of the matrix.

Wound therapy apparatus 200 may be periodically varied between first stage of operation 236 and second stage of operation 238 by consecutive withdrawal of output fluid 218 from enclosed space 217 and input of input fluid 216 into enclosed space 217 via lumen 245 of port 242. At exemplary first stage of operation 236, as illustrated in FIG. 6A, the target pressure $p_0$ equals the maximum pressure $p_{max}$ (i.e., $p_0 = p_{max}$), the maximum pressure may be generally equal to ambient pressure $p_{amb}$ (i.e., $p_{max} \approx p_{amb}$), and the actual pressure $p_a$ generally equals the target pressure $p_0$ (i.e., $p_a \approx p_0$) within enclosed space 217. Wound bed 213 is in a baseline state 293, and is in spaced relation with pad 250 such that there is reduced contact or no contact between pad 250 and wound bed 213. The gap, if any, between pad 250 and wound bed may vary depending on the shape, structure and material used to make pad 250. As illustrated in FIG. 6A, wound interface 215 defines entry 226 to enclosed space 217, and the portions of wound bed 213 enclosed by enclosed space 217 may generally lie outside entry 226 in baseline state 293. Capillary 296, which is proximate wound bed 213, is undilated in baseline condition 297 and conveys a baseline quantity of blood to wound bed 213 in baseline condition 297 at first stage of operation 236, as illustrated in FIG. 6A.

At exemplary second stage of operation 238 of appliance 200, as illustrated in FIG. 6B, enclosed space 217 is evacuated, in part, by withdrawal of output fluid 218 from enclosed space 217 through lumen 245 of port 242 so that the target pressure $p_0 = p_{min}$ and the actual pressure $p_a$ generally equals the target pressure $p_0$ within enclosed space 217. Pressure $p_{min}$ is less than ambient pressure $p_{amb}$ (i.e. $p_{min} < p_{amb}$) by an amount sufficient to cause at least portions of wound bed 213 to be distended into enclosed space 217 through entry 226 in distended state 294. At least portions of wound bed, or a greater portion of wound bed 213 than in first stage of operation 236 biases against pad 250 at second stage of operation 238, as illustrated in FIG. 6B. Pad 250 may thus effectively absorb and transfer exudate from wound bed 213 through lumen 245 as at least a portion of output fluid 218 at second stage of operation 238. Pad 250 fluidly communicates with lumen 245 of port 242 so that exudate may be evacuated through and from pad 250 through lumen 245 as at least a portion of output fluid 218 via external suction applied to port 242. Capillary vessels proximate the wound bed, such as capillary 296, may be in a dilated state 298 when wound bed 213 is in distended state 294 at second stage of operation 238, as illustrated in FIG. 6B.

A problem, for example, is the clogging of the output tubing by exudate, leading to a falsely reassuring reading of target suction pressure being maintained by the control package when a much lower actual suction pressure, if any, exists at the wound site. By adding an additional port that is also in independent communication with enclosed space 217, differential pressure readings can be obtained of the same enclosed space from the front end and back end of a pressure conduit system that may enable more accurate diagnosis, and may localize problem situation to allow more targeted solutions or prophylactic actions. The additional port may be situated a distance apart from the first port, with both ports in fluid communication with the wound. Furthermore, when a bolus of fluid is introduced via the second port to abruptly relieve the suction pressure within the enclosed space, such sudden one-way pressure relief may serve to blast purge exudate out of the suction port, from one end of the wound bed to the other, unclog tubing, maintain tubing patency, and help to maintain effective therapy. Using an irrigant as a liquid bolus provided added benefit of further rinses away any condensed exudate, cellular debris and keep lines open. When used in conjunction with a dressing system in which the input relief port is near one end of the absorbent pad and the suction port is near the other end, intermittent use of irrigant to relieve suction may extend the clinically serviceable life of such a dressing system not unlike a self-cleaning diaper in that exudate and cellular debris is rinsed away and the dressing is "refreshed". Aside from replacement cost savings, other benefits may include a lower incidence of adhesive tape allergy which is often precipitated by the repeated and concomitant loss of a layer of epidermis with each dressing change; the epidermal layer insulates the underlying dermis layer from being exposed to the adhesive.

FIG. 7 illustrates wound therapy apparatus 300 including wound interface 315. Appliance 300 includes structure 315, and structure 315 includes covering 320 attached to skin surface 311 by adhesive 390 to enclose wound bed 313 at skin surface 311, with the entirety of wound boundary 312 covered by covering 320. Distal side 322 of covering 320 faces wound bed 313 with covering 320 in securement to skin surface 311 by adhesive 390 on at least portions of distal side 322 of covering 320, thereby defining portions of enclosed space 317. Enclosed space 317 includes at least portions of wound bed 313, as illustrated. Dressing 350 is placed against wound bed 313 and sealingly covered by covering 320, as illustrated, so that dressing 350 lies within enclosed space 317, as illustrated.

As illustrated in FIG. 7, ports 342, 344 are in fluid communication with enclosed space 317 between distal side 322 of covering 320 and proximal side 324 of covering 320 by lumen 345, 347, respectively.

Lumen 345, 347 in fluid communication with a control group, such as control group 30, 130 of wound therapy apparatus 10, 100, respectively, and the control group may regulate the input of input fluid 316 into enclosed space 317 through lumen 345 and regulate the withdrawal of output fluid 318 from enclosed space 317 through lumen 347, in this implementation. Exudate 352 migrates from wound bed 313 into dressing 350, and exudate 352 may be withdrawn from dressing 350 as part of output fluid 318, in this implementation.

For example, input fluid 316 may be input into enclosed space 317 via lumen 347 of port 342 and output fluid 318 may be withdrawn from enclosed space 317 via lumen 345 of port 344 as actual pressure $p_a$ within enclosed space 317 is varied in conformance to target pressure $p_0$. For example, target pressure $p_0$ may be periodically varied over the pressure range $p_{min} \leq p_0 \leq p_{max}$ where $p_{min}$ is the minimum target pressure over the pressure cycle and $p_{max}$ is the maximum target pressure over the pressure cycle, and the actual pressure $p_a$ is conformed to the target pressure $p_0$.

Figure 8:
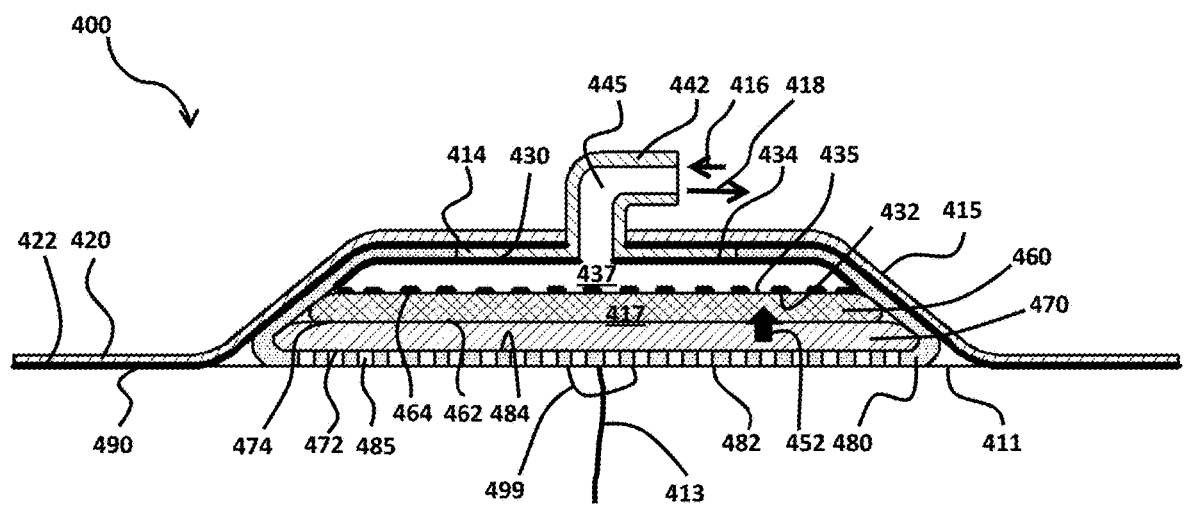
FIG. 8 illustrates by cut-away elevation view a fifth exemplary implementation of a wound interface.

FIG. 8 illustrates exemplary wound therapy apparatus 400. As illustrated in FIG. 8, wound therapy apparatus 400 includes wound interface 415, and wound interface 415 includes member 420 with adhesive 490 coated on at least portions of distal surface 422 of member 420 for securing member 420 to skin surface 411. When secured to skin surface 411, distal surface 422 of member 420 encloses wound bed 413 at skin surface 411 within enclosed space 417. Member 420 may be formed of various polymers such as, for example, polyurethane. Member 420 may be fluid-tight and member 420 may be deformation resistant.

As illustrated in FIG. 8, flange 414 of port 442 secures port 442 to member 420 for fluid communication with enclosed space 417 by lumen 445. The flange may be adhesively secured to the underside of pad 420 via an aperture in pad 420 as shown, or it may be adhesively secured on the upper and outer surface of member 420 and fluidly communicate with the enclosed space 437 within the wound interface via an aperture or connecting passageway.

Input fluid 416 may be input into enclosed space 417 via lumen 445 of port 442 and output fluid 418 may be withdrawn from enclosed space 417 via lumen 445 of port 442. Lumen 445 may be in fluid communication with a control group, such as control group 30, 130 of wound therapy apparatus 10, 100, respectively. The control group may regulate the input of input fluid 416 into enclosed space 417 through lumen 445 and regulate the withdrawal of output fluid 418 from enclosed space 417 through lumen 445, in this implementation, for example, to conform actual pressure $p_a$ with target pressure $p_0$ as target pressure $p_0$ within enclosed space 417 is, for example, periodically varied according to a pressure cycle generally having a pressure range $p_{min} \leq p_0 \leq p_{max}$ where $p_{min}$ is the minimum target pressure over the pressure cycle and $p_{max}$ is the maximum target pressure over the pressure cycle.

As illustrated in FIG. 5, appliance 400 includes layers 460, 470, and 480 within enclosed space 417. Portions of layer 480, as illustrated, are secured to distal side 422 of member 420, and portions of distal side 482 of layer 480 are biased against skin surface 411 and wound bed 413. Layer 470 is biased between layer 480 and layer 460 with distal side 472 of layer 470 biased against proximal side 484 of layer 480, and proximal side 474 of layer 470 biased against distal side 462 of layer 460. Layer 460 is biased between layer 470 and spacer 430 with proximal side 474 of layer 470 biased against distal side 432 of spacer 430. Various numbers of layers, such as layers 460, 470, 480, may be included in other implementations of appliance 400, and the layers may be arranged in various ways, or certain layers omitted, depending on application. Different layers may have special characteristics and functions, such as, for example, liquid absorption, fluid transfer, and release of therapeutic substances.

Proximal side 434 of spacer 430 is secured to distal side 422 of member 420 within enclosed space 417, in this implementation. Spacer 430 defines void 437 within spacer 430, and spacer 430 maintains layers 460, 470, 480 in biased engagement with one another, as illustrated. Spacer 430 may generally be a bilayer polymer pouch with or without additional distribution channels within that may be created by localized bonding or welding 464. It may optionally be welded at multiple points 464 in the bilayer space to limit distension of the void 437 when under pressure. The purpose of spacer 430 is to disperse input fluid 416 across the entire wound surface. Spacer 430 may have a variety of sizes and shapes such as circular, rectangular, ovoid, or starburst, with a perimeter that substantially approximates that of proximal side 464 of layer 460.

Lumen 445 passes through port 442 and through proximal side 434 of spacer 430 into void 437, and input fluid 416 may be communicated via lumen 445 into void 437 or output fluid 418 may be communicated from void 437 through lumen 445.

For example, input fluid 416 may be communicated into void 437 through lumen 445, and input fluid 416 may then disperse within void 437 so that essentially the same pressure actual pressure $p_a$ exists throughout void 437. Input fluid 416 may then flow from void 437 through spacer passages in distal side 432 of spacer 430, such as spacer passage 435, into layer 460. The spacer passages may be evenly distributed over distal side 432 of spacer 430 so that input fluid 416 is evenly distributed over proximal side of layer 460 from void 437. Input fluid 416 may then flow through layer 460, through layer 470, and through perforations, such as perforation 485, in layer 480 to contact wound bed 413 as well as skin surface 411. The perforations, which pass between proximal side 484 and distal side 482 of layer 480, may be evenly distributed over layer 480 so that input fluid 416 is evenly distributed over skin surface 411 and wound bed 413. Thus, for example, input fluid 416 may, for example, provide enhanced $O_2$ exposure, antibiotic rinse, or cytokines in the form of amniotic fluid to wound bed 413 and to skin surface 411. The actual pressure $p_a$ exists throughout enclosed space 417 including wound bed 413 and skin surface 411, and input fluid 416 and output fluid 418 may flow throughout enclosed space 417 including layers 460, 470, 480 and through spacer 430. The spacer 430 may optionally be structured more distally to be closer to or even adjacent the wound surface, in which case, spacer passages 435 may be present in both the distal and proximal sides of spacer 430.

Exudate 452 may flow from wound bed 413 through layer passages, such as layer passages 485 in layer 480, into layer 470, from layer 470 into layer 460, and from layer 460 through spacer passages, such as spacer passage 435, into void 437. Output fluid 418 including exudate 452 may flow from layers 480, 470 460 through spacer passages 435 into void 437, and output fluid 418 may be withdrawn from void 437 through port 442 via lumen 445, in this implementation.

In this implementation, layer 480 is formed of silicone, including similar materials with scar modulation properties, and wound bed 413 has the form of an incision with stitch 499. Silicone, as used herein, includes siloxane, various polysiloxanes, silicone-like materials, and various combinations thereof that may be generally solid. Silicone may have the chemical formula $[R_2SiO]_n$, where R is an organic group. Silicone may include, for example, silicone polymers having an average molecular weight in excess of 100,000 (e.g., between about 100,000 and about 10,000,000). Examples may include, but are not limited to, crosslinked siloxanes (e.g., crosslinked dimethicone or dimethicone derivatives), copolymers such as stearyl methyl-dimethyl siloxane copolymer, polysilicone-11 (a crosslinked silicone rubber formed by the reaction of vinyl terminated silicone and (methylhydro dimethyl)polysiloxane in the presence of cyclomethicone), cetearyl dimethicone/vinyl dimethicone crosspolymer (a copolymer of cetearyl dimethicone crosslinked with vinyl dimethyl polysiloxane), dimethicone/phenyl vinyl dimethicone crosspolymer (a copolymer of dimethylpolysiloxane crosslinked with phenyl vinyl dimethylsiloxane), and dimethicone/vinyl dimethicone crosspolymer (a copolymer of dimethylpolysiloxane crosslinked with vinyl dimethylsiloxane).

Wound bed 413 may be any type of wound bed, and layer 480 may be formed of other polysiloxane or similar materials, in various other implementations. Perforations 485 may take a range of forms, ranging from small holes, crosses, to slits, and allow fluid exchange with wound bed 413 and skin surface 411 through layer 480, to prevent maceration of skin 411.

Layer 470 may include a layer of material that delivers therapeutics in a slow release manner. Such therapeutics may include antimicrobials such as antibiotic or silver formulations, local anesthetic for pain reduction, amniotic or placental derived cytokines and growth factors such as BMP, hemostatics and coagulants to stop bleeding, oxygen generating and releasing compounds, exo-or endothermic reagents, etc.

Layer 460 may be made of a variety of materials including cotton gauze, polyester or polyamide fibers, or open-cell foams of polyurethane or polyvinyl alcohol. These materials of layer 460 may aid in transfer of exudate 452 from the wound bed 413 to void 437 for removal through lumen 445. Layer 460 may optionally include a super absorbent polymer such as sodium polyacrylate, especially when the intent is to lock the exudate 452 within layer 460.

In operation of a wound therapy apparatus, such as wound therapy apparatus 10, 100, 200, 300, 400, target pressure $p_0$ within an enclosed space, such as enclosed space 17, 117, 217, 317, 417, of a wound interface, such as wound interface 15, 115, 215, 315, 415, may be varied with respect to time t according to a pressure cycle, such as exemplary pressure cycle 500, 550, 600, 650, 700, 750, 800, 850, 900, 950 (see FIGS. 9A, 9B, 9C, 9D, 9E, 9F, 9G, 9H, 9I, 9J, respectively) and the actual pressure $p_a$ within the enclosed space of the wound interface may be conformed to the target pressure $p_0$ so that $p_a \approx p_0$ by controlling the input of input fluid, such as input fluid 16, 116, 216, 316, 416 into the enclosed space of the wound interface, and by controlling the withdrawal of output fluid, such as output fluid 18, 118, 218, 318, 418, out of the enclosed space of the wound interface using a control group, such as control group 30, 130. The input fluid may be gas, such as gas 22, 125, or liquid, such as liquid 24, in various implementations. The output fluid may include exudate, such as exudate 19, 152, 252, 352, 452, and any residual gas or liquid from a previous pressure cycle, or any combination thereof.

Exemplary pressure cycles 500, 550, 600, 650, 700, 750, 800, 850, 900, 950 are illustrated in FIGS. 9A, 9B, 9C, 9D, 9E, 9F, 9G, 9H, 9I, 9J, respectively, in which the target pressure $p_0$ within the enclosed space of the wound interface is graphed as a function of time t. Although pressure cycles 500, 550, 600, 650, 700, 750, 800, 850, 900, 950 are describe in terms of target pressure $p_0$, the actual pressure $p_0$ may generally corresponds to target pressure $p_0$ within the enclosed space, so that pressure cycles 500, 550, 600, 650, 700, 750, 800, 850, 900, 950 may be descriptive of the behavior of the actual pressure $p_a$ within the enclosed space. Because the input fluid, in various implementations, has an $O_2$ concentration greater than atmospheric air, the wound bed is exposed to fluid with $O_2$ concentration greater than atmospheric air throughout the pressure cycles, in various implementations, which may increase the oxygen supply to the wound bed during therapy with resulting therapeutic benefits. The application of multiple pressure cycles to the wound bed with $O_2$ concentration greater than atmospheric air may increase the 02 exposure of the wound bed and thus the time of oxygen therapy delivered to the wound bed. Note that pressure cycles 500, 550, 600, 650, 700, 750, 800, 850, 900, 950 are exemplary only and not limiting, and one or more of these exemplary pressure cycles, various combinations of these exemplary pressure cycles or other pressure cycles may be delivered to the wound bed within the enclosed space as controlled by the control group 130, in various implementations.

The control group, in various implementations, includes a controller, such as controller 87, 165, and the pressure cycle including period, amplitude, and other characteristics of the pressure cycle may be based upon data, such as data 74, communicated to the controller from a user I/O, such as user I/O 86, 145, by a user. Accordingly, the user may select the pressure cycle(s) to be delivered to the wound bed within the enclosed space, a sequence of the pressure cycles, and characteristics such as amplitude and period of the pressures cycles using the user I/O. The controller may have preprogrammed pressure cycles in memory, and the controller may include other programs or data in memory to determine the pressure cycle(s) from the data and to implement the pressure cycle(s) using a pump, such as pump 89, 168, valve(s), such as valve 88, 172, 173, 174, and pressure sensor(s), such as pressure sensor 91, 176, 178, as may be included in the control group.

Figure 9A:
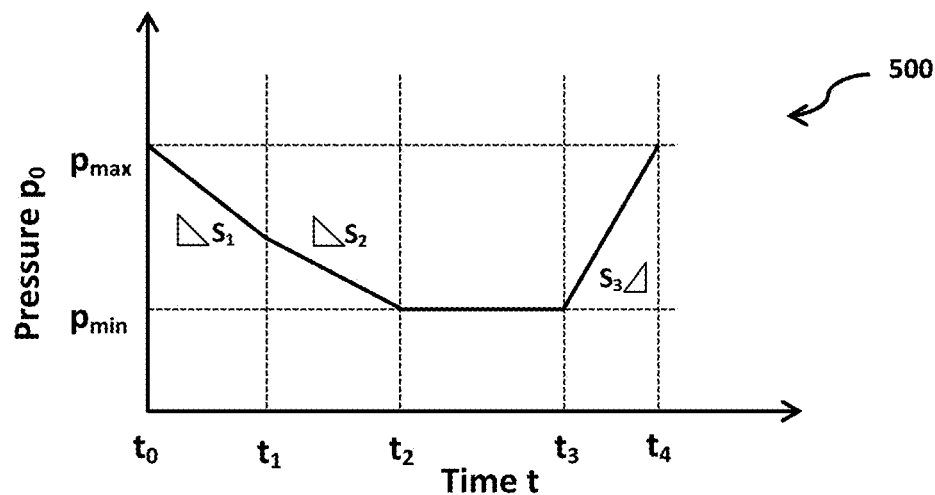
FIG. 9A illustrates by Cartesian plot an exemplary pressure cycle as may be delivered to a wound bed by the wound therapy apparatus, such as the exemplary wound therapy apparatus of FIGS. 2, 3A, 6A, 7, and 8.

As illustrated in FIG. 9A, pressure cycle 500 is initiated at time $t_0$ and target pressure $p_0=p_{max}$. Note that actual pressure $p_a$ within the enclosed space as controlled by the control group may be generally equal to target pressure $p_0$ throughout pressure cycle 500 (i.e., $p_a \approx p_0$). According to exemplary pressure cycle 500, target pressure $p_0$ reduces linearly at rate $S_1$ from time $t_0$ to time $t_1$, and then target pressure $p_0$ reduces linearly at rate $S_2$ between time $t_1$ and time $t_2$ reaching $p_{min}$ at time $t_2$. Target pressure $p_0$ is then maintained at $p_{min}$ between time $t_2$ and time $t_3$, and then target pressure $p_0$ increases linearly at rate $S_3$ from $p_{min}$ to $p_{max}$ between time $t_3$ and time $t_4$, as illustrated. Input fluid input into the enclosed space between time $t_3$ and time $t_4$ to increase the pressure $p_a$ from $p_{min}$ to $p_{max}$ may have an $O_2$ concentration greater than that of atmospheric air. Accordingly, the wound bed may be exposed to $O_2$ at a concentration greater than that found in atmospheric air during successive pressure cycles 500 when the pressure in each such pressure cycle is increased by fluid having an $O_2$ concentration greater than that of atmospheric air. The wound bed, in this example, may, thus, be exposed to $O_2$ concentration greater than that of atmospheric air at pressure $p_{max}$ between time $t_3$ and time $t_4$.

The control group may reduce the actual pressure $p_a$ between times $t_0$ and $t_2$ by withdrawal of output fluid from the enclosed space without any concurrent input of input fluid into the enclosed space. Similarly, the control group may increase the actual pressure $p_a$ between times $t_3$ and $t_4$ by input of input fluid into the enclosed space without any concurrent withdrawal of output fluid from the enclosed space. Finally, there is no input of input fluid into the enclosed space and concurrent withdrawal of output fluid from the enclosed space between times $t_2$ and $t_3$, in various implementations of pressure cycle 500. Essentially no fluid is input into the enclosed space and essentially no fluid other than exudate, is withdrawn from the enclosed space between time $t_2$ and time $t_3$, in various implementations of pressure cycle 500. A controller, such as controller 480 of wound therapy apparatus 400, may control the withdrawal of output fluid between times $t_0$ and $t_2$ and the input of input fluid between times $t_3$ and $t_4$.

In pressure cycle 500, for example, $p_{max}=p_{amb}$ and $p_{min}=/p_{amb}-85$ mm Hg. The time period $t_2-t_0$ may be approximately 40 s, and target pressure $p_0$ is then held at $p_{min}$ for $t_3-t_2=240$ s, followed by time period $t_4-t_3=80$ s, so that the period of pressure cycle 500 is $t_4-t_0=360$ s (6 minutes or 10 pressure cycles per hour). In various other implementations, the control group may deliver, for example 12 pressure cycles per hour, 4 pressure cycles per hour, or 3 pressure cycles per hour, according to exemplary pressure cycle 500. Slopes $S_1$ and $S_2$ may be selected to avoid creating pain and $S_2$ may be less than $S_1$, as rapid decreases below $p_{max}$ in target pressure $p_0$ may be painful. For example, decreasing the target pressure $p_0$ from ambient pressure $p_{amb}$ to $p_{amb}-40$ mm Hg over time period $t_1-t_0=10$ s with corresponding decrease in the actual pressure $p_a$ may be generally pain free followed by decreasing the target pressure $p_0$ to $p_{amb}-85$ mm Hg over $t_2-t_1=30$ s again to attempt to minimize pain. Note that pressure cycle 500 may be asymmetrical with time $t_3-t_0$ being greater than time $t_4-t_3$.

In various other implementations, target pressure $p_0$ may change at a single constant rate between time $t_0$ and time $t_2$ ($S_1=S_2$) or target pressure $p_0$ may change at three or more rates between time $t_0$ and time $t_2$. Pressure cycle 500 may repeat starting at time $t_4$ (i.e. time $t_4$ is set to time to), or some other pressure cycle, such as pressure cycle 550, 600, 650, 700, 750, 800, 850, 900, 950 may then be initiated starting at time $t_4$. Pressure cycle 500 may remain essentially unchanged over successive cycles, or various parameters of pressure cycle 500, such as $p_{max}$, $p_{min}$, $S_1$, $S_2$, $t_3-t_2$, $t_4-t_0$, may be altered over successive cycles. The control group may determine the various parameters of pressure cycle 500, such as $p_{max}$, $p_{min}$, $S_1$, $S_2$, $t_3-t_2$, $t_4-t_0$, using data communicated from the user I/O, the data being input into the user I/O by the user.

Figure 9B:
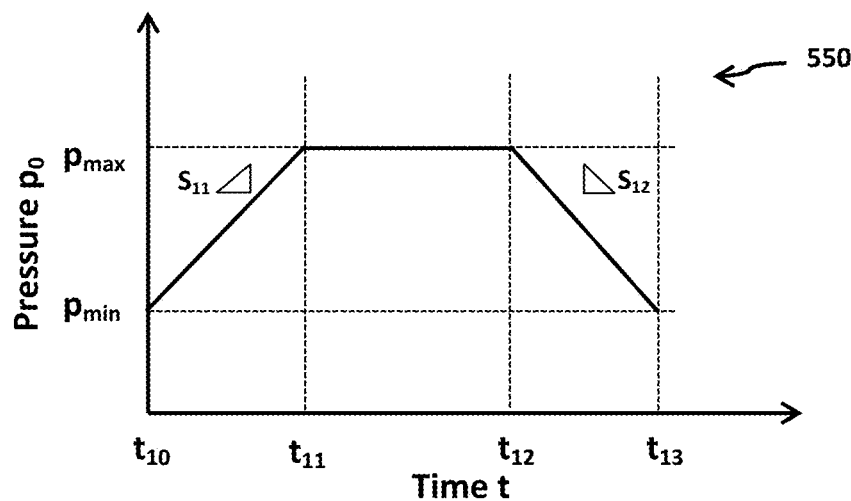
FIG. 9B illustrates by Cartesian plot a second exemplary pressure cycle as may be delivered to a wound bed by the wound therapy apparatus, such as the exemplary wound therapy apparatus of FIGS. 2, 3A, 6A, 7, and 8.

An exemplary pressure cycle 550 is illustrated in FIG. 9B. Note that actual pressure $p_a$ within the enclosed space as controlled by the control group may be generally equal to target pressure $p_0$ throughout pressure cycle 550 (i.e., $p_a \approx p_0$). As illustrated in FIG. 9B, pressure cycle 550 is initiated at time $t_{10}$ and target pressure $p_0=p_{min}$. Target pressure $p_0$ increases linearly at rate $S_{11}$ from time $t_{10}$ to time $t_{11}$ reaching $p_{max}$ at time $t_{11}$. Target pressure $p_0$ is then maintained at $p_{max}$ between time $t_{11}$ and time $t_{12}$, and then target pressure $p_0$ decreases linearly at rate $S_{12}$ from $p_{max}$ to $p_{min}$ between time $t_{12}$ and time $t_{13}$, as illustrated. Input fluid input into the enclosed space between time $t_{10}$ and time $t_{11}$ in order to increase the actual pressure $p_a$ from $p_{min}$ to $p_{max}$ may have an $O_2$ concentration greater than that of atmospheric air. Accordingly, the wound bed may be exposed to enhanced oxygen at actual pressure $p_a$ greater than $p_{min}$ for time period $t_{13}-t_{10}$ in exemplary pressure cycle 550. Because generally $p_{amb} \leq p_{max}$ the wound bed may be exposed to enhanced oxygen at actual pressure $p_a$ generally greater than or equal to ambient pressure $p_{amb}$ for time period $t_{12}-t_{11}$, in exemplary pressure cycle 550.

The actual pressure $p_a$ within the enclosed space may be increased between times $t_{10}$ and $t_{11}$ by input of input fluid into the enclosed space without any concurrent withdrawal of output fluid from the enclosed space. Similarly, the actual pressure $p_a$ within the enclosed space may be decreased between times $t_{12}$ and $t_{13}$ by withdrawal of output fluid from the enclosed space without any concurrent input of input fluid into the enclosed space. The control group may control the input of input fluid between times $t_{10}$ and $t_{11}$ and the withdrawal of output fluid between times $t_{12}$ and $t_{13}$. Finally, there is no input of input fluid into the enclosed space and concurrent withdrawal of output fluid from the enclosed space between times $t_{11}$ and $t_{12}$, in various implementations of pressure cycle 550.

In pressure cycle 550, for example, $p_{max}=p_{amb}+40$ mm Hg and $p_{min}=p_{amb}$, approximately. The time period $t_{11}-t_{10}$ may be approximately 40 s, and target pressure $p_0$ is then held at $p_{max}$ approximately for $t_{12}-t_{11}=240$ s, followed by time period $t_{13}-t_{10}=80$ s approximately, so that the period of pressure cycle 550 is $t_{13}-t_{10}=360$ s (6 minutes or 10 pressure cycles per hour). The pressure $p_{max}$ of pressure cycle 550 may be limited, for example in certain embodiments, by the ability of the adhesive, such as adhesive 190, 290, 390, 490 to secure the wound interface to a skin surface, such as skin surface 211, 311, 411, under pressure $p_{max}$, which forces the wound interface 15 away from the skin surface.

Pressure cycle 550 may repeat starting at time $t_{13}$ (i.e., time $t_{13}$ is set to time $t_{10}$), or some other pressure cycle, such as pressure cycle 500, 600, 650, 700, 750, 800, 850, 900, 950 may then be initiated starting at time $t_{13}$. Pressure cycle 550 may remain essentially unchanged over successive cycles, or various parameters of pressure cycle 550, such as $p_{max}$, $p_{min}$, $S_{11}$, $S_{12}$, $t_{11}-t_{10}$, $t_{12}-t_{11}$, $t_{13}-t_{12}$, may be altered over successive cycles.

For example, in certain implementations, the control group may deliver several pressure cycles according to pressure cycle 550 and then a pressure cycle according to pressure cycle 500 so that the actual pressure $p_a$ varies generally over pressures greater than ambient pressure $p_{amb}$ to deliver enhanced oxygen (hyperbaric) to the wound bed and the actual pressure $p_a$ varies over pressures less than ambient pressure $p_{amb}$ that may remove exudate from the wound bed or reseal the adhesive of the wound interface to the skin surface. In general, several minutes of pressurized topical oxygen such as around 40 mm Hg, which is well below MAP (mean arterial perfusion pressure) may be beneficial. Pressure cycles 500, 550 may be combined, for example, so that time period $t_{13}-t_{10}$ is about 4 minutes and time period $t_4-t_0$ is about 2 minutes to deliver hyperbaric therapy to the wound bed for about ⅔ of the pressure cycle period of 6 minutes and to deliver suction therapy for about ⅓ of the pressure cycle period. When pressure cycles 500, 550 are so combined, the resultant pressure cycle is asymmetric with more time period spent delivering hyperbaric therapy and less time period spent delivering suction therapy, in this example.

Figure 9C:
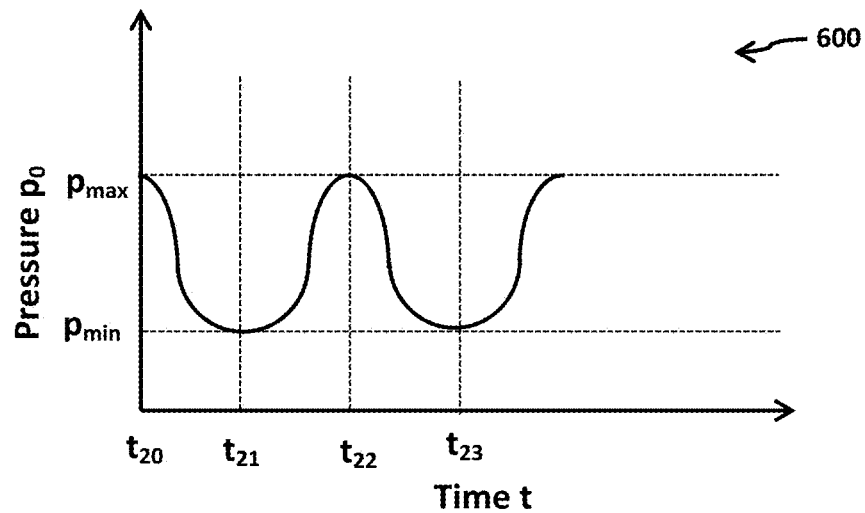
FIG. 9C illustrates by Cartesian plot a third exemplary pressure cycle as may be delivered to a wound bed by the wound therapy apparatus, such as the exemplary wound therapy apparatus of FIGS. 2, 3A, 6A, 7, and 8.

Another exemplary pressure cycle 600 is illustrated in FIG. 9C, and actual pressure $p_a$ may be generally equal to target pressure $p_0$ throughout pressure cycle 600. In exemplary pressure cycle 600, target pressure $p_0$ decreases and increases continuously in a sinusoidal (non-linear) manner, as illustrated in FIG. 9C, and, thus actual pressure $p_a$ decreases and increases continuously in a sinusoidal manner. As illustrated in FIG. 9C, pressure cycle 600 is initiated at time $t_{20}$ and target pressure $p_0=p_{max}$. In this implementation, target pressure $p_0$ decreases from time $t_{20}$ to time $t_{21}$ reaching $p_{min}$ at time $t_{21}$, target pressure $p_0$ then increases from $p_{min}$ to $p_{max}$ between time $t_{21}$ and time $t_{22}$, and then pressure $p_0$ decreases from $p_{max}$ to $p_{min}$ between time $t_{22}$ and time $t_{23}$. In exemplary pressure cycle 600, target pressure $p_0$ decreases and increases continuously, as illustrated. Pressure cycle 600 may repeat any number of times. Pressure cycle 600 may remain essentially unchanged over successive cycles, or various parameters of pressure cycle 600, such as $p_{max}$, $p_{min}$, or the period $t_{22}-t_{20}$, may be altered over successive cycles. In other implementations, the target pressure $p_0$ may increase in a sinusoidal manner, then maintained at a constant $p_{max}$ for some time period, and finally decreasing in a sinusoidal manner.

Figure 9D:
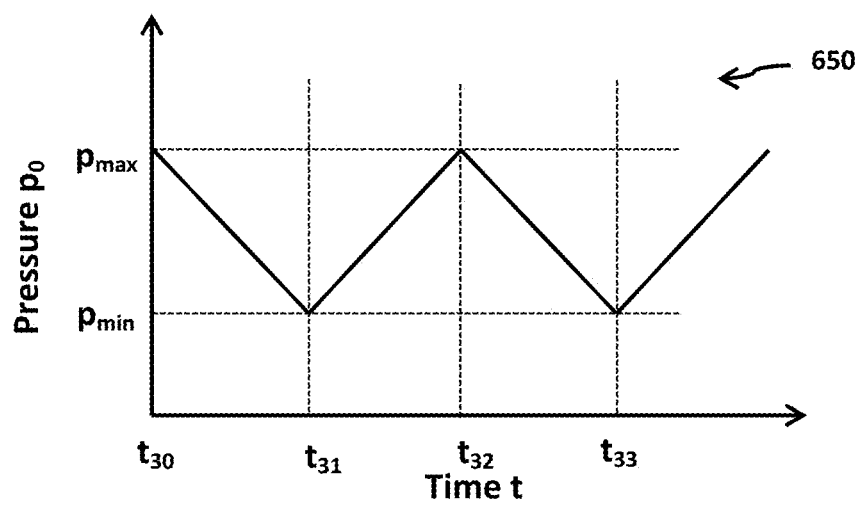
FIG. 9D illustrates by Cartesian plot a fourth exemplary pressure cycle as may be delivered to a wound bed by the wound therapy apparatus, such as the exemplary wound therapy apparatus of FIGS. 2, 3A, 6A, 7, and 8.

Another exemplary pressure cycle 650 is illustrated in FIG. 9D. In exemplary pressure cycle 650, target pressure $p_0$ decreases and then increases continuously as a triangular waveform, as illustrated in FIG. 7D, and actual pressure $p_a$ may be generally equal to target pressure $p_0$ throughout pressure cycle 650. As illustrated in FIG. 9D, pressure cycle 650 is initiated at time $t_{30}$ and target pressure $p_0 \approx p_{max}$. In this implementation, target pressure $p_0$ decreases linearly from time $t_{30}$ to time $t_{31}$ reaching $p_{min}$ at time $t_{31}$, and then target pressure $p_0$ increases linearly from $p_{min}$ to $p_{max}$ between time $t_{31}$ and time t32 thus completing one pressure cycle. The next pressure cycle starts with target pressure $p_0$ decreasing linearly from time t32 to time $t_{33}$ reaching $p_{min}$ at time $t_{33}$. In exemplary pressure cycle 650, target pressure $p_0$ decreases and then increases continuously as a triangular waveform, as illustrated. Pressure cycle 650 may repeat any number of times. The input fluid input to increase the actual pressure $p_a$ to $p_{max}$ by the control group may include $O_2$ at a concentration greater than that found in atmospheric air, and such increased $O_2$ may be delivered several times in succession by successive waveforms thereby exposing the wound bed continuously to an oxygen rich environment.

Figure 9E:
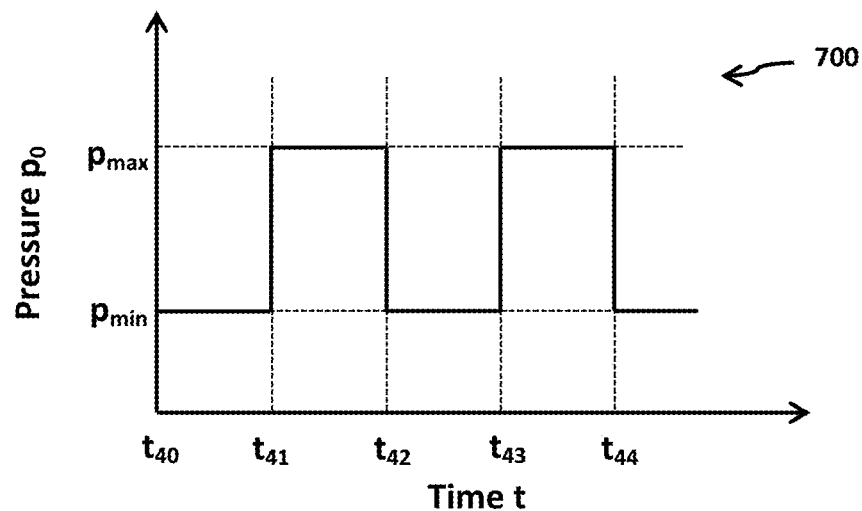
FIG. 9E illustrates by Cartesian plot a fifth exemplary pressure cycle as may be delivered to a wound bed by the wound therapy apparatus, such as the exemplary wound therapy apparatus of FIGS. 2, 3A, 6A, 7, and 8.

Another exemplary pressure cycle 700 is illustrated in FIG. 9E. As illustrated in FIG. 9E, target pressure $p_0$ is altered stepwise (pulsatile) between $p_{min}$ to $p_{max}$ and actual pressure $p_a$ within the enclosed space is altered in correspondence to target pressure $p_0$ throughout pressure cycle 700 by the control group. The stepwise increase in target pressure $p_0$ from $p_{max}$ to $p_{max}$ in pressure cycle 700 may blow any residual exudate out of lumen in communication with the enclosed space, such as lumen 245, 345, 347, 445, including fluid pathways in communication with the lumen in order to eliminate blockages caused by solidification therein of exudate including medicaments and other materials that may solidify.

It is a commonly encountered problem for the thick proteinaceous exudate from the wound bed to become increasingly concentrated, forming a plug and occlude the lumen including fluid pathways in communication with the lumen. When this happens, not only does exudate withdrawal cease, the exudate plug interferes with pressure sensing. This impedes therapy and the entire wound interface may have to be changed prematurely, assuming medical personnel are available to do so, resulting in increased cost and added pain to the patient. In order to solve this problem, in various implementations, the end of a pressure cycle may be initiated by a sudden or abrupt release of pressure prim, towards ambient pressure $p_{amb}$ by the infusion of a bolus of gas or liquid This may prevent the creation of line-occluding exudate plugs, or if they do form, result in the forced expulsion of an exudate plug by pressure alone or in combination with liquid dissolution. The result may be the elimination or prevention of intra-lumen occlusion and more accurate sensing and delivery of suction therapy.

In various implementations, the control group may deliver pulses of input fluid, in conformance to pressure cycle 700 to remove blockages from the lumen including fluid pathways in communication with the lumen or the enclosed space. This may maintain the patency of the suction tubing and enable accurate sensing of target pressure $p_0$ within the enclosed space. The magnitude of the step may be produced for example, by a high fluid flow rate or by a high-compliance reservoir balloon that is interposed between the fluid source and valve that regulates flow delivered to the enclosed space. The maximum pressure $p_{max}$ should be less than pressure that could breach the fluid-tightness of the wound interface. This is dependent on a number of factors including the characteristics of the adhesive that is used to anchor the wound interface to the skin. In general, such pulsed maximum pressure $p_{max}$ may be less than about 30-40 mm Hg above ambient pressure $p_a$.

Figure 9F:
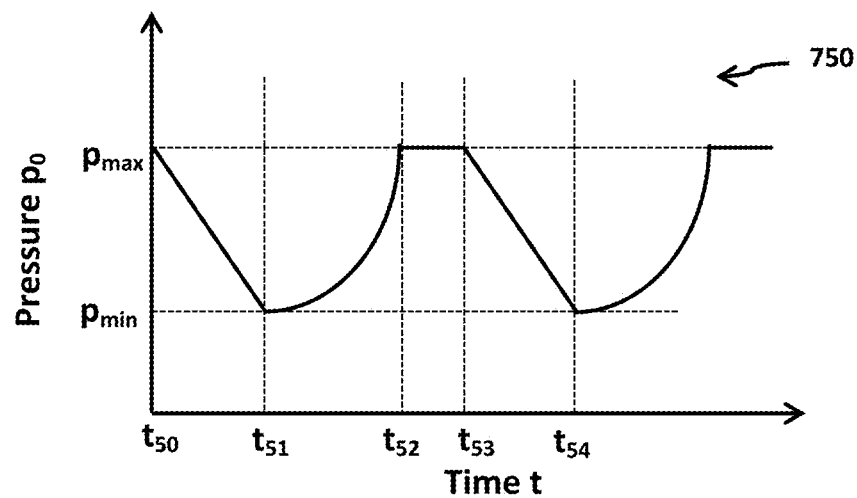
FIG. 9F illustrates by Cartesian plot a sixth exemplary pressure cycle as may be delivered to a wound bed by the wound therapy apparatus, such as the exemplary wound therapy apparatus of FIGS. 2, 3A, 6A, 7, and 8.

Another exemplary pressure cycle 750 is illustrated in FIG. 9F. As illustrated in FIG. 9F, target pressure $p_0$ decreases linearly from $p_{max}$ to $p_{min}$ and then target pressure $p_0$ increases exponentially (non-linearly) from $p_{min}$ to $p_{max}$. Actual pressure $p_a$ may be generally equal to target pressure $p_0$ throughout pressure cycle 750. In exemplary pressure cycle 750, fluid with oxygen concentration greater than that of atmospheric air may be input between times $t_{52}$ and $t_{51}$ to increase the actual pressure $p_a$ from $p_{min}$ to $p_{max}$, and the actual pressure $p_a$ is then maintained constant at $p_{max}$ for time period $t_{53}$–$t_{52}$ to deliver oxygen to the wound bed at pressure $p_{max}$ for time period $t_{53}$–$t_{52}$. The cycle 750 repeats starting at time $t_{53}$ with linear decrease in target pressure $p_0$ from $p_{max}$ to $p_{min}$ between times $t_{53}$ and $t_{54}$ followed by exponential increase in target pressure $p_0$ from $p_{min}$ to $p_{max}$, as illustrated in FIG. 9F.

Figure 9G:
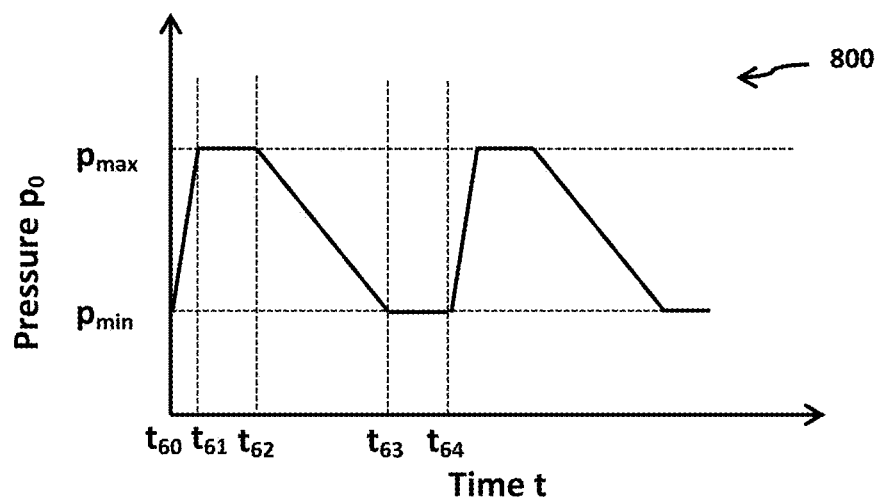
FIG. 9G illustrates by Cartesian plot a seventh exemplary pressure cycle as may be delivered to a wound bed by the wound therapy apparatus, such as the exemplary wound therapy apparatus of FIGS. 2, 3A, 6A, 7, and 8.

Another exemplary pressure cycle 800 is illustrated in FIG. 9G. Actual pressure $p_a$ may be generally equal to target pressure $p_0$ throughout pressure cycle 800, and target pressure $p_0$ varies linearly from $p_{min}$ to $p_{max}$ and from $p_{max}$ to $p_{min}$, as controlled by the control group. Fluid with oxygen concentration greater than that of atmospheric air may be input by the control group between times $t_{60}$ and $t_{61}$ to increase the actual pressure $p_a$ to maximum pressure $p_{max}$. Target pressure $p_0$ and, thus, actual pressure $p_a$ is maintained constant at $p_{max}$ for time period $t_{62}$–$t_{61}$, for example to deliver oxygen at pressure $p_{max}$ to the wound bed, in this exemplary pressure cycle. Target pressure $p_0$ is maintained constant at $p_{min}$ for time period $t_{64}$–$t_{63}$, for example to withdraw exudate from the wound bed, in exemplary pressure cycle 800.

Figure 9H:
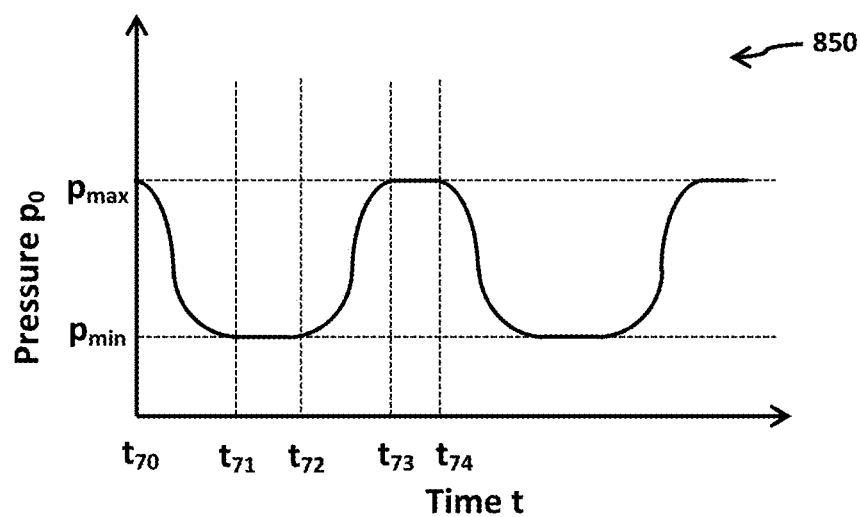
FIG. 9H illustrates by Cartesian plot an eighth exemplary pressure cycle as may be delivered to a wound bed by the wound therapy apparatus, such as the exemplary wound therapy apparatus of FIGS. 2, 3A, 6A, 7, and 8.

Another exemplary pressure cycle 850 is illustrated in FIG. 9H. As controlled by the control group, actual pressure $p_a$ may be generally equal to target pressure $p_0$ throughout pressure cycle 850, and target pressure $p_0$ varies sinusoidally from $p_{max}$ to $p_{min}$ and from $p_{min}$ to $p_{max}$, in exemplary pressure cycle 850. Target pressure $p_0$ is maintained constant at $p_{min}$ for time period $t_{72}$–$t_{71}$ for example to deliver oxygen at pressure $p_{max}$ to the wound bed, and target pressure $p_0$ is maintained constant at $p_{max}$ for time period $t_{74}$–$t_{73}$ for example to withdraw exudate from the wound bed, in exemplary pressure cycle 850.

Figure 9I:
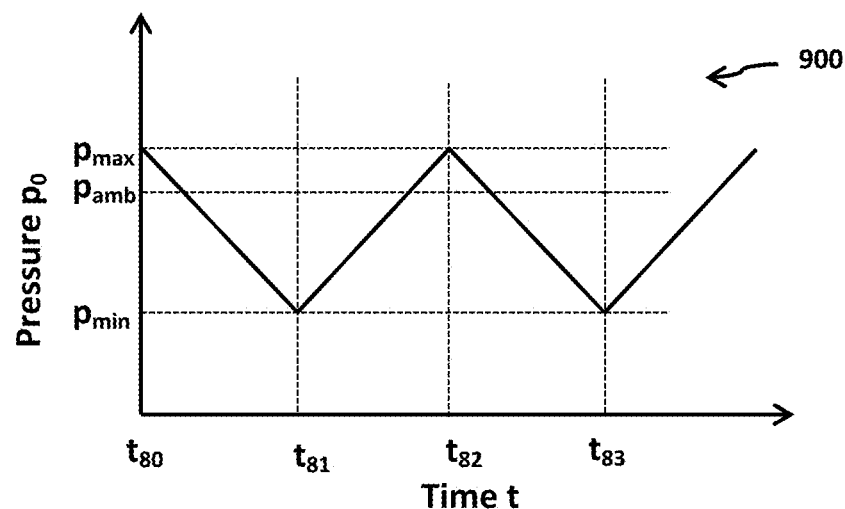
FIG. 9I illustrates by Cartesian plot a ninth exemplary pressure cycle as may be delivered to a wound bed by the wound therapy apparatus, such as the exemplary wound therapy apparatus of FIGS. 2, 3A, 6A, 7, and 8.

In exemplary pressure cycle 900, illustrated in FIG. 9I, target pressure $p_0$ decreases and increases continuously linearly in a sawtooth pattern, and actual pressure $p_a$ may be generally equal to target pressure $p_0$ throughout pressure cycle 900. Note that maximum pressure $p_{max}$ is greater than ambient pressure $p_{amb}$ in exemplary pressure cycle 900.

Figure 9J:
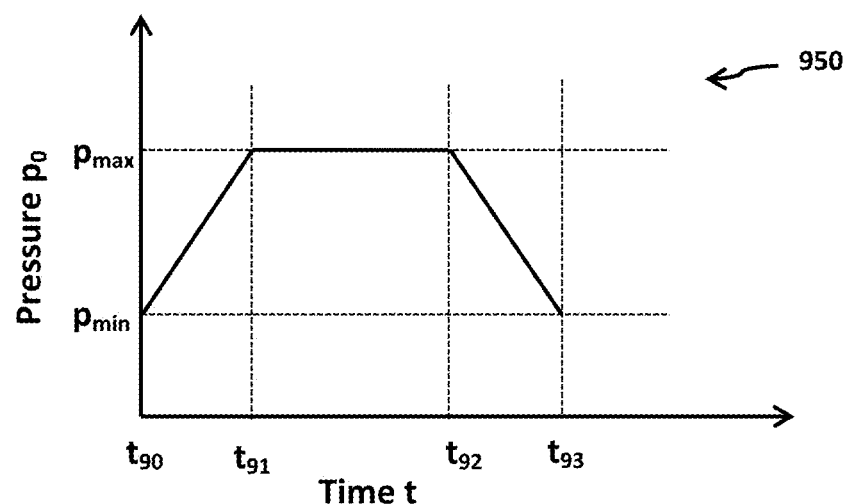
FIG. 9J illustrates by Cartesian plot a tenth exemplary pressure cycle as may be delivered to a wound bed by the wound therapy apparatus, such as the exemplary wound therapy apparatus of FIGS. 2, 3A, 6A, 7, and 8.

In exemplary pressure cycle 950, illustrated in FIG. 9J, pressure $p_0$ is initially at $p_{min}$ at time $t_{90}$. The control group increases the actual pressure $p_a$ in conformance with the target pressure $p_0$ from $p_{min}$ to $p_{max}$ between times $t_{90}$ and $t_{91}$ by input of input fluid as liquid into the enclosed space. The control group controls the inputting of liquid as the input fluid and withdrawal of the liquid as at least a portion of the output fluid, in this implementation. The liquid, which forms at least a portion of the input fluid in this implementation, may provide various therapeutic benefits. The liquid may include, for example, saline solution, proteolytic enzyme solution, biofilm degradation solution, antibiotic lavage, amniotic fluid, platelet-enriched plasma, antibiotic, anesthetic, or other liquid having therapeutic benefits. In various implementations, 50 cc or more of liquid may be input into the enclosed space between times $t_{90}$ and $t_{91}$. The input fluid in the form of liquid remains within the enclosed space between times $t_{91}$ and $t_{92}$ to provide a therapeutic benefit to the wound bed, and the liquid is then generally withdrawn from the enclosed space including any pad, such as pad 250, 450 or dressing, such as dressing 350, within the enclosed space as the actual pressure $p_a$ in correspondence to the target pressure $p_0$ is decreased from $p_{max}$ to $p_{min}$ between times $t_{92}$ and $t_{93}$. The therapeutic benefit may include debridement, in various implementations.

The decrease in target pressure $p_0$ between times $t_{92}$ and $t_{93}$ may mark the beginning of a pressure cycle such as, for example, pressure cycle 500, 550, 600, 650, 700, 750, 850, 900. The decrease in target pressure $p_0$ from $p_{max}$ to $p_{min}$ between times $t_{92}$ and $t_{93}$ may remove 90% or more of the liquid from the enclosed space including any dressing, pad, or layers, such as layers 460, 470, 480, disposed therein, in certain implementations. Time period $t_{92}$–$t_{91}$ during which the liquid is within the enclosed space at pressure $p_{max}$ may range, for example, from about 2 minutes to about 1 hour. Time periods $t_{92}$–$t_{91}$ of less than 1 hour or time periods $t_{92}$–$t_{91}$ of only a few minutes may prevent maceration particularly when the skin surface is coated with adhesive such as cyanoacrylate. No input of input fluid into the enclosed space or withdrawal of output fluid from the enclosed space may occur between times $t_{91}$ and $t_{92}$, i.e., there is no flow through the enclosed space between times $t_{91}$ and $t_{92}$, in some implementations.

In other implementations, liquid may pass through the enclosed space as input fluid and output fluid simultaneously i.e., the liquid is simultaneously input and withdrawn between times $t_{91}$ and $t_{92}$. Pressure cycle 950, for example, may be intermittently interposed between other pressure cycles, such as pressure cycle 500, 550, 600, 650, 700, 750, 800, 850, 900, or pressure cycle 950 may be repeated several times in succession.

The wound therapy apparatus may deliver a therapy regimen to the wound bed. The therapy regimen may include a sequence of pressure cycles of the actual pressure $p_a$ within the enclosed space in conformance to target pressure $p_0$. The pressure cycles may be, for example, any of exemplary pressure cycles 500, 550, 600, 650, 700, 750, 800, 850, 900, 950 and the sequence of pressure cycles may include several consecutive pressure cycles.

Example I

Example I presents series of pressure cycles as used in exemplary wound therapy regimens delivered to the wound bed by the wound therapy apparatus. Example I demonstrates an exemplary application of these exemplary wound therapy regimens to wound therapy of the wound bed.

In this Example, the pad or the dressing may be omitted from the wound bed during at least portions of the healing process. The absence of the pad or dressing eliminates the need for dressing change and the associated pain and inhibition of the healing processes due to disruption of granulation tissue as well as the attendant costs for medical personnel and various consumables, and may allow for visual inspection of the wound bed and surrounding skin through transparent portions of the wound interface. Because no dressing or pad is used in this implementation, the wound therapy apparatus may be employed until complete healing of the wound bed is achieved. The absence of the dressing or pad, except, perhaps, in the initial exudative phase of wound bed, may permit, for example, lavage of wound bed as well as incubation of stem cells incubation of tissue stroma, proteolytic enzyme soaks, medical maggot debridement or a skin graft. The wound therapy apparatus may be employed until complete healing of the wound bed is achieved.

In Example I, N designates a pressure therapy according to exemplary pressure cycle 500 with gas having $O_2$ concentration greater than atmospheric air input into the enclosed space between times $t_3$ and $t_4$ to increase the actual pressure $p_a$ within the enclosed space to $p_{max}$. Note that humidity may be added to the gas or to other gas(es) in various pressure cycles to prevent drying of the wound bed. O designates a therapy according to exemplary pressure cycle 550 with $O_2$ input into the enclosed space between $t_{10}$ and $t_{11}$ in order to increase the pressure within the enclosed space to $p_{max}$ with $p_{max}$ being greater than ambient pressure $p_{amb}$ in pressure cycle 550 as used in Example I.

Therapy Regimens which are groups of four pressure cycles (four therapies) are as follows:
  Therapy Regimen 1—N/N/N/N (four consecutive N therapies)
  Therapy Regimen 2—N/N/N/O (three consecutive N therapies followed by one O therapy)
  Therapy Regimen 3—N/O/N/O (N therapy alternating with O therapy)
  Therapy Regimen 4—O/O/O/N (three O therapies followed by an N therapy that may reattached the wound interface to the skin surface)

If each pressure cycle (either O therapy or N therapy) is delivered over 6 minutes, for example, each Therapy Regimen is then delivered over 24 minutes allowing the Therapy Regimen to be delivered 60 times a day. In general, at the early phase of wound treatment, relatively speaking, more N therapy may be used, as in exemplary Therapy Regimen 1 and exemplary Therapy Regimen 2, in order to remove exudate, such as exudate 51, 151, 251, 351, 419, and improve circulation. Once the exudative phase is over, the need for N therapy is diminished. At this point the therapy regimen may switch to N/O/N/O as in exemplary Therapy Regimen 3, and, lastly, O therapy would become the dominant therapy. An occasional N therapy may be interposed with a series of O therapies, as in exemplary Therapy Regimen 4, to reseat the wound interface onto the skin. An exemplary week of prescribed therapy Regimens may be:
  Days 1-2: Therapy Regimen 1
  Days 3-4: Therapy Regimen 2
  Day 5-6: Therapy Regimen 3
  Day 7: Therapy Regimen 4

Therapy Regimen 1, which is all N therapy, is used at the initiation of wound therapy, per Example I, as interstitial edema with large quantities of exudate may be present. The negative target pressures $p_0$ of Therapy Regimen 1 may draw the exudate from the wound bed and may reduce the edema by withdrawing exudate from the wound bed that causes the edema. After two days of Therapy Regimen 1, the wound therapy changes from Therapy Regimen 1 to Therapy Regimen 2 that interposes O therapy with the N therapy. The use of gas having $O_2$ concentration greater than atmospheric air under target pressure $p_0$ generally greater than or equal to ambient pressure $p_{amb}$ to deliver $O_2$ to the wound bed in the O therapy may aid in healing while the N therapy may continue to treat the edema by withdrawing exudate from the wound.

After two days of Therapy Regimen 2, the wound therapy changes from Therapy Regimen 2 to Therapy Regimen 3 that alternates O therapy with the N therapy as the wound continues to heal. The use of gas having $O_2$ concentration greater than atmospheric air in the O therapy may aid in healing while the continued N therapy may continue to treat the edema by withdrawing exudate from the wound.

Finally, at Day 7 per Example I, the wound therapy changes from Therapy Regimen 3 to Therapy Regimen 4, which is predominantly O therapy with one cycle of N therapy every four cycles. The negative pressures of the N therapy may re-adhere the wound interface to the skin thereby prolonging the life of the fluid-tight seal between the wound interface and the skin surface.

Depending on the duration and magnitude of O therapy, a possibility exists for the seal between the wound interface and skin surface to become threatened or even breached. Loss of integrity of the seal, which would allow inflow of outside air during subsequent suction cycles, may dehydrate wound tissue and be detrimental for wound healing. To prevent this occurrence, aside from selecting a suitable maximum pressure $p_{max}$ and duration, ending a sequence of O therapy with at least a brief N therapy may allow the adhesive of the wound interface to be reseated and, thus, re-secured to the skin surface. The ratio of frequency of such negative pressure cycles in relation to the positive pressure cycles may be 1:1, 1:2 or some other suitable ratio depending on a number of parameters, including the duration and magnitude of the positive pressure cycle.

Once the wound interface is unable to maintain a fluid tight seal (typically due to skin shedding or adhesive failure), the wound interface may require replacement. Replacement is estimated to be once every 5 to 7 days depending on the location of the wound bed and individual variability. Note that a pressure cycle such as pressure cycle 950 may be included from time $t_0$ time in any of Therapy Regimen 1, Therapy Regimen 2, Therapy Regimen 3, Therapy Regimen 4 to provide liquid to the wound bed. The liquid may be, for example, saline solution, proteolytic enzyme solution, biofilm degradation solution, antibiotic lavage, amniotic fluid, platelet-enriched plasma, antibiotic, anesthetic, or other liquid having therapeutic benefits.

Thus, in Example I, the progression is from initial use of N therapy that treats edema, to a mix of N therapy with O therapy that both treats edema and promotes healing, and, finally, to predominantly O therapy that promotes healing as the wound bed heals and the edema subsides. For example, Therapy Regimen 4 may be used when the wound is at least halfway healed and there is no longer any significant exudate.

It is assumed in Example 1 for explanatory purposes that the wound bed heals progressively between Day 1 and Day 7. Of course, healing may require other than a week, and, accordingly, the various Therapy Regimens, such as Therapy Regimens 1, 2, 3, and 4, may be continued for various lengths of time and may be combined as appropriate depending upon the condition of the wound bed. Therapy Regimens 1, 2, 3, and 4, may be linked with one another or with other Therapy Regimens in various ways, in various implementations. In other implementations, the Therapy Regimens, such as Therapy Regimens 1, 2, 3, 4, may have other patterns of pressure cycles, for example, O/O/O/O/. The Therapy Regimens, in other implementations, may have various numbers and types of cycles, such as pressure cycle 500, 550, 600, 650, 700, 750, 800, 850, 900, 950.

The wound therapy apparatus may deliver liquid into the enclosed space of the wound interface as directed by the control group the including controller, and the liquid may have various therapeutic purposes. Operations of the wound therapy apparatus may include selecting the liquid from a liquid source, such as liquid source 84, as the input fluid. Operations of the wound therapy apparatus may include controlling the input of input fluid into the enclosed space of the wound interface or controlling the withdrawal of output fluid out of the enclosed space of the wound interface using the control group in ways appropriate to the therapeutic purpose. For example, liquid as input fluid may be input into the enclosed space and then withdrawn from the enclosed space as output fluid to irrigate the wound bed in order to remove bio-burden or to moisturize the wound bed. As another example, liquid as input fluid may be input into the enclosed space and allowed to remain within the enclosed space when the liquid has healing or antiseptic properties. As yet another example, liquid as input fluid may be input into the enclosed space and withdrawn from the enclosed space as output fluid in order to flush out various fluid pathways through which input fluid or output fluid are communicated. Input of liquid or withdrawal of liquid from the enclosed space may be user selected by data communicated to the controller using the user I/O. Input of liquid or gas may be user selected by data communicated to the controller 65 by the user using the user I/O.

Figure 10:
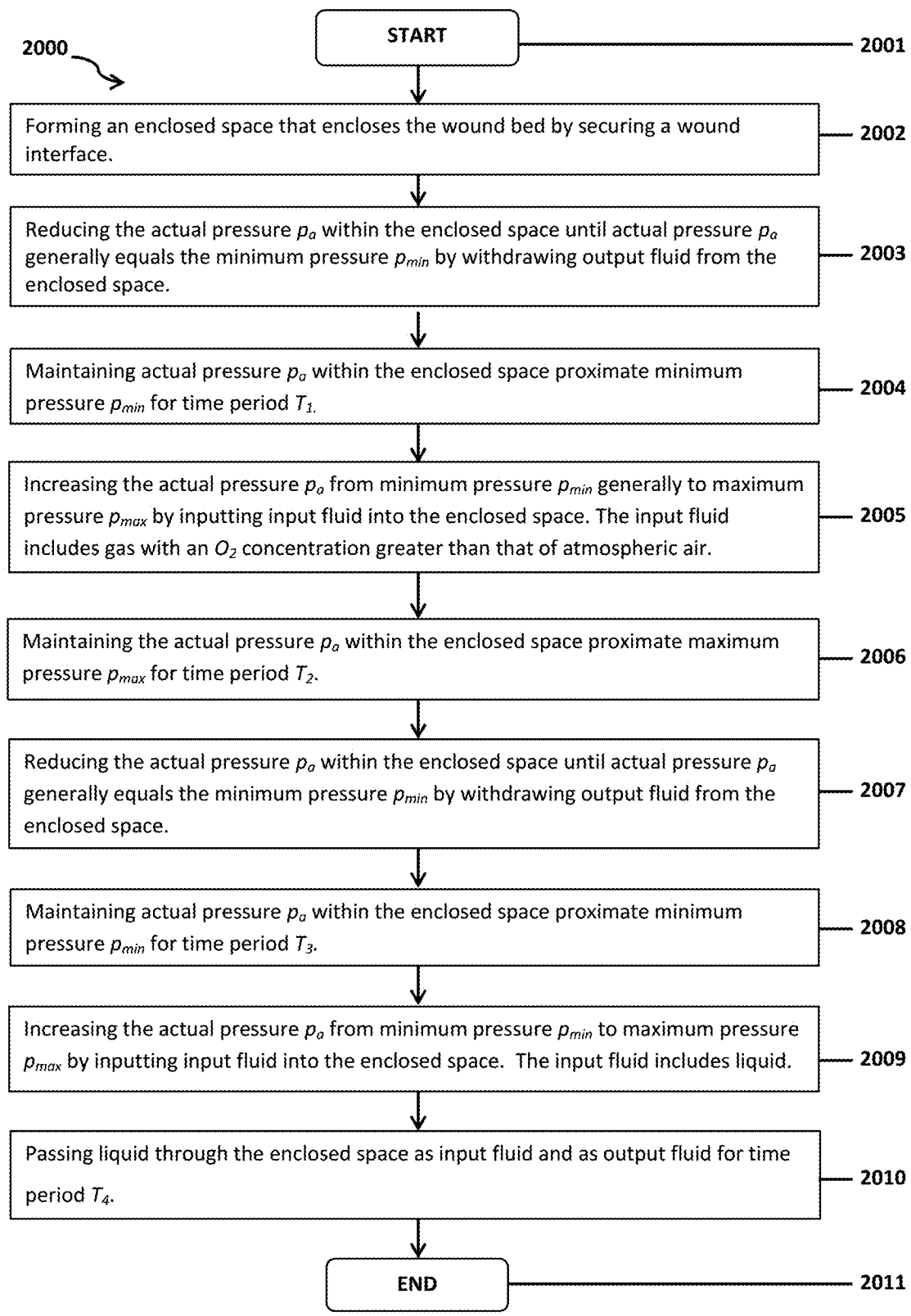
FIG. 10 illustrates by process flow chart an exemplary method of use of the wound therapy apparatus such as the exemplary wound therapy apparatus of FIGS. 2, 3A, 6A, 7, and 8.

Another exemplary method of use of the wound therapy apparatus is illustrated by process flow chart in FIG. 10. Operational method 2000 as illustrated in FIG. 10 and the associated description is exemplary only. As illustrated in FIG. 10, operational method 2000 is entered at step 2001. At step 2002, the wound interface of the wound therapy apparatus is secured to the skin surface forming the enclosed space over the wound bed. At step 2003, output fluid is withdrawn from the enclosed space thereby reducing the actual pressure $p_a$ within the enclosed space until actual pressure $p_a$ generally equals the minimum pressure $p_{min}$. Actual pressure $p_a$ within the enclosed space may then be maintained proximate minimum pressure $p_{min}$ for time period $T_1$, as per step 2004. For example, time period $T_1$ may be about 3 to 5 minutes. At step 2005, input fluid is input into the enclosed space thereby increasing the actual pressure $p_a$ from minimum pressure $p_{min}$ to maximum pressure $p_{max}$. The input fluid input into the enclosed space at exemplary step 2005 to increase generally the actual pressure $p_a$ from minimum pressure $p_{min}$ to maximum pressure $p_{max}$, comprises a gas with an $O_2$ concentration greater than that of atmospheric air.

At step 2006, the maximum pressure $p_{max}$ may be about ambient pressure $p_{amb}$, the maximum pressure $p_{max}$ may be greater than ambient pressure $p_{amb}$, or the maximum pressure $p_{max}$ may be less than ambient pressure $p_{amb}$, in various implementations. Actual pressure $p_a$ within the enclosed space may then be maintained proximate maximum pressure $p_{max}$ for time period $T_2$, as per exemplary step 2006. For example, time period $T_2$ may be about 1-3 minutes.

As illustrated in FIG. 10, output fluid is withdrawn from the enclosed space at step 2007 to reduce the actual pressure $p_a$ within the enclosed space until actual $p_a$ generally equals the minimum pressure $p_{min}$. Actual pressure $p_a$ within the enclosed space may then be maintained proximate minimum pressure $p_{min}$ for time period $T_3$, as per step 2008. Because the fluid input into the enclosed space at step 2005 comprises a gas with an $O_2$ concentration greater than that of atmospheric air, the wound bed is exposed to gas with an $O_2$ concentration greater than that of atmospheric air throughout steps 2006, 2007, and 2008, in exemplary operational method 2000.

At step 2009, input fluid is input into the enclosed space to increase the actual pressure $p_a$ from minimum pressure $p_{min}$ to maximum pressure $p_{max}$. The input fluid at step 2009 comprises liquid, in exemplary operational method 2000.

Output fluid is withdrawn from the enclosed space and input fluid is input into the enclosed space sequentially by the wound therapy apparatus in performing steps 2003, 2004, 2005, 2006, 2007, 2008 and 2009, in exemplary operational method 2000, so that either input fluid is being input or output fluid is being withdrawn. Input fluid is not input at the same time output fluid is being withdrawn in performing steps 2003, 2004, 2005, 2006, 2007, 2008 and 2009 of exemplary operational method 2000.

At step 2010, liquid is then passed through the enclosed space for time period $T_4$. The liquid may be sequentially input into the enclosed space and then withdrawn from the enclosed space or the liquid may be simultaneously input into the enclosed space and withdrawn from the enclosed space, at step 2010. Liquid may be input in pulses to purge blockages within various passages that fluidly communicate with the enclosed space, at step 2010. At step 2010, for example, the liquid may flush out the enclosed space including the wound bed and dressing, remove bioburden or exudate, cleanse the wound bed, hydrate the wound bed. At step 2010, the liquid may be input and withdrawn by instillation (steady flow). The control group may limit the actual pressure $p_a$ of the liquid within the enclosed space for example to about ambient pressure $p_{amb}$ in order to prevent dislodgement of the wound interface. For example, when actual pressure $p_a$ of the liquid within the enclosed space generally equals ambient pressure $p_{amb}$ as detected by the pressure sensor, the control group may reduce or stop the input of liquid into the enclosed space.

Exemplary operational method 2000 then terminates at step 2011. Exemplary method 2000 may be repeated any number of times with various combinations of steps 2003, 2004, 2005, 2006, 2007, 2008, 2009, 2010. Note that minimum pressure $p_{min}$ and maximum pressure $p_{max}$ may change between steps 2003, 2004, 2005, 2006, 2007, 2008, 2009, 2010, and times $T_1$, $T_2$, $T_3$, $T_4$ as well as minimum pressure $p_{min}$ and maximum pressure $p_{max}$ may be altered during various repetitions of method 2000.

Methods of wound therapy may include the step of engaging the wound interface with the skin surface around the wound bed thereby defining the enclosed space over the wound bed. Methods of wound therapy may include the steps of establishing fluid communication between the wound interface, the control group, the liquid source, and the gas source. Methods of wound therapy may include the step of regulating the input of input fluid into the enclosed space in sequence with regulating the withdrawal of output fluid from the enclosed space using the control group operably controlled by a the controller thereby altering the actual pressure $p_a$ within the enclosed space in correspondence to target pressure $p_0$, the pressure cycle having minimum pressure $p_{min}$ and maximum pressure $p_{max}$, the input fluid comprising a gas having an $O_2$ concentration greater than atmospheric air.

Methods of wound therapy may include the step of removing exudate from the output fluid by flowing the output fluid through a reservoir, such as reservoir 81, 150.

Methods of wound therapy may include the step of receiving data using the I/O interface in operable communication with the controller, and communicating the data to the controller thereby altering the pressure cycle or altering the input fluid between liquid and gas.

Methods of wound therapy may include the step of delivering a therapy regimen to the wound bed, the therapy regimen comprising a series of pressure cycles of the actual pressure $p_a$ within the enclosed space.

Methods of wound therapy may include the step of delivering a therapy regimen to the wound bed, the therapy regimen comprising inputting liquid into the enclosed space and may include the step of withdrawing liquid from the enclosed space.

Methods of wound therapy may include the programmed delivery of various gasses and liquids to the wound bed as controlled by the controller.

Methods of wound therapy may include the step of delivering air to the enclosed space when other gasses and liquids are unavailable. Methods of wound therapy include the step of delivering gas to the enclosed space to produce actual pressure $p_a$ within the enclosed space equal to ambient pressure $p_{amb}$ in the event of power failure of the wound therapy device. The foregoing discussion along with the Figures discloses and describes various exemplary implementations. These implementations are not meant to limit the scope of coverage, but, instead, to assist in understanding the context of the language used in this specification and in the claims. The Abstract is presented to meet requirements of 37 C.F.R. § 1.72(b) only. The Abstract is not intended to identify key elements of the methods of use and of apparatus disclosed herein or to delineate the scope thereof. Upon study of this disclosure and the exemplary implementations herein, one of ordinary skill in the art may readily recognize that various changes, modifications and variations can be made thereto without departing from the spirit and scope of the inventions as defined in the following claims.

What is claimed is:

1. A wound therapy apparatus, comprising:
a wound interface that defines an enclosed space over a wound bed that is fluid tight when secured to a skin surface around the wound bed; and
a control group that cooperates with the wound interface to regulate input of input fluid comprising a gas having an $O_2$ concentration greater than atmospheric air into the enclosed space and to regulate the withdrawal of output fluid from the enclosed space in order to vary an actual pressure $p_a$ within the enclosed space generally between a minimum pressure $p_{min}$ and a maximum pressure $p_{max}$, and in order to vary the actual pressure $p_a$ intermediate of the minimum pressure $p_{min}$ and the maximum pressure $p_{max}$ in substantial continuous conformance to a target pressure $p_0$ specified continuously as a function of time.

2. The apparatus of claim 1, wherein the minimum pressure $p_{min}$ is greater than an ambient pressure $p_{amb}$.

3. The apparatus of claim 1, wherein the maximum pressure $p_{max}$ is greater than an ambient pressure $p_{amb}$.

4. The apparatus of claim 1, wherein the input fluid further comprises a liquid.

5. The apparatus of claim 4, wherein the liquid as input fluid is input into the enclosed space as a pulse to remove exudate within lumen in fluid communication with the enclosed space.

6. The apparatus of claim 1, wherein the input fluid further comprises a nitric oxide gas.

7. A wound therapy apparatus, comprising:
a wound interface attachable to a skin surface around a wound bed to define an enclosed space over the wound bed that is fluid tight; and
a control group that cooperates with a liquid source of a liquid, a gas source of a gas, and the enclosed space to deliver an input fluid into the enclosed space and to withdraw an output fluid from the enclosed space in order to vary an actual pressure $p_a$ within the enclosed space generally between a minimum pressure $p_{min}$ and a maximum pressure $p_{max}$, and in order to vary the actual pressure $p_a$ intermediate of the minimum pressure $p_{min}$ and the maximum pressure $p_{max}$ in substantial continuous conformance to a target pressure $p_0$ specified continuously as a function of time throughout a pressure cycle, the input fluid selected from a group consisting of the liquid and the gas.

8. The apparatus of claim 1, wherein the minimum pressure $p_{min}$ is greater than an ambient pressure $p_{amb}$.

9. The apparatus of claim 1, wherein the gas has an $O_2$ concentration greater than atmospheric air.

10. The apparatus of claim 1, wherein the gas comprises nitric oxide.

11. A method for wound therapy, comprising the steps of:
attaching a wound interface to a skin surface around a wound bed thereby defining an enclosed space over the wound bed that is fluid tight;
specifying a target pressure $p_0$ within the enclosed space as a continuous function of time throughout a pressure cycle;
regulating the input of input fluid into the enclosed space using a control group and regulating the withdrawal of output fluid from the enclosed space using the control group thereby altering an actual pressure $p_a$ within the enclosed space between a minimum pressure $p_{min}$ and a maximum pressure $p_{max}$ while substantially continuously conforming the actual pressure $p_a$ intermediate of the minimum pressure $p_{min}$ and the maximum pressure $p_{max}$ with the target pressure $p_0$ throughout the pressure cycle; and
wherein the input fluid comprises a gas.

12. The method of claim 11, further comprising the step of:
delivering a therapy regimen to the wound bed, the therapy regimen comprising several of the pressure cycles.

13. The method of claim 11, wherein the minimum pressure $p_{min}$ is greater than an ambient pressure $p_{amb}$.

14. The method of claim 11, wherein the maximum pressure $p_{max}$ is greater than an ambient pressure $p_{amb}$.

15. The method of claim 11, wherein the gas has an $O_2$ concentration greater than atmospheric air.

16. The method of claim 11, wherein the gas comprises nitric oxide.

17. The method of claim 11, wherein the input fluid further comprises a liquid.

* * * * *